(12) United States Patent
Rosenberg et al.

(10) Patent No.: US 7,094,752 B2
(45) Date of Patent: Aug. 22, 2006

(54) PEPTIDE LIGANDS OF THE UROKINASE RECEPTOR

(75) Inventors: Steven Rosenberg, Oakland, CA (US); Michael V. Doyle, Oakland, CA (US); Harold A. Chapman, Newton, MA (US)

(73) Assignees: Chiron Corporation, Emeryville, CA (US); Brigham and Women's Hospital Harvard Medical School, Boston, MA (US)

( * ) Notice: Subject to any disclaimer, the term of this patent is extended or adjusted under 35 U.S.C. 154(b) by 238 days.

(21) Appl. No.: 10/821,544

(22) Filed: Apr. 9, 2004

(65) Prior Publication Data

US 2004/0265797 A1    Dec. 30, 2004

Related U.S. Application Data

(62) Division of application No. 09/155,260, filed as application No. PCT/US97/05199 on Mar. 28, 1997, now Pat. No. 6,794,358.

(51) Int. Cl.
*A61K 38/04* (2006.01)
*C07K 7/04* (2006.01)

(52) U.S. Cl. ............................ 514/2; 530/300; 530/350
(58) Field of Classification Search ...................... None
See application file for complete search history.

(56) References Cited

U.S. PATENT DOCUMENTS 5,519,120 A    5/1996  Dano et al.
5,656,726 A    8/1997  Rosenberg et al.

OTHER PUBLICATIONS

Goodson, et al., "High-affinity urokinase receptor antagonists identified with bacteriophage peptide display", Proc. Natl. Acad. Sci. USA, vol. 91, pp. 7129-7133, Jul. 1994.
Ploug et al., "Structure-function relationships in the receptor for urokinase-type plasminogen activator"—"Comparison to other members of the Ly-6 family and snake venom α-neurotoxins", FEBS Letters 349 (1994) 163-168.
Wei, et al., "Identification of the Urokinase Receptor as an Adhesion Receptor for Vitronectin", The Journal of Biological Chemistry, vol. 269, No. 51, Issue of Dec. 23, pp. 32380-32388, 1994.
Doyle et al., (1996) Fibrinolysis 10:21.
Bowie et al., (1990) Science 247: 1307-1310.
Waltz, et al., "Reversible cellular adhesion to vitronection linked to urokinase receptor occupancy", J Biol Chem, May 20, 1994, 269 (20), p14746-50.

*Primary Examiner*—Michael Pak
(74) *Attorney, Agent, or Firm*—James E. Austin; Young J. Suh; Alisa A. Harbin

(57) ABSTRACT

Novel peptides that are capable of binding to uPAR and inhibiting the binding of an integrin and vitronectin are described. Also provided are nucleic acid sequences encoding the novel peptides. Methods for screening for small molecules, other peptides, or peptoids that mimic the antagonistic function of the peptides of the invention are described. The invention has applications in design of therapeutics for treating disorders characterized by upregulation of uPA and uPAR, and cancer and chronic inflammation, cell migration or uPAR: integrin binding interactions, and diagnostical applications to such disorders.

4 Claims, 6 Drawing Sheets

Vitronectin DQESCKGRCTEGFNVDKKCQcDELcsYYQSCCTDYTAECKPQVtRGD

Clone 7  AE PVYQYELDsYLRSYY

Clone 18  AELDLStFYDIQYLLRT

FIG. 3

Figure 1:
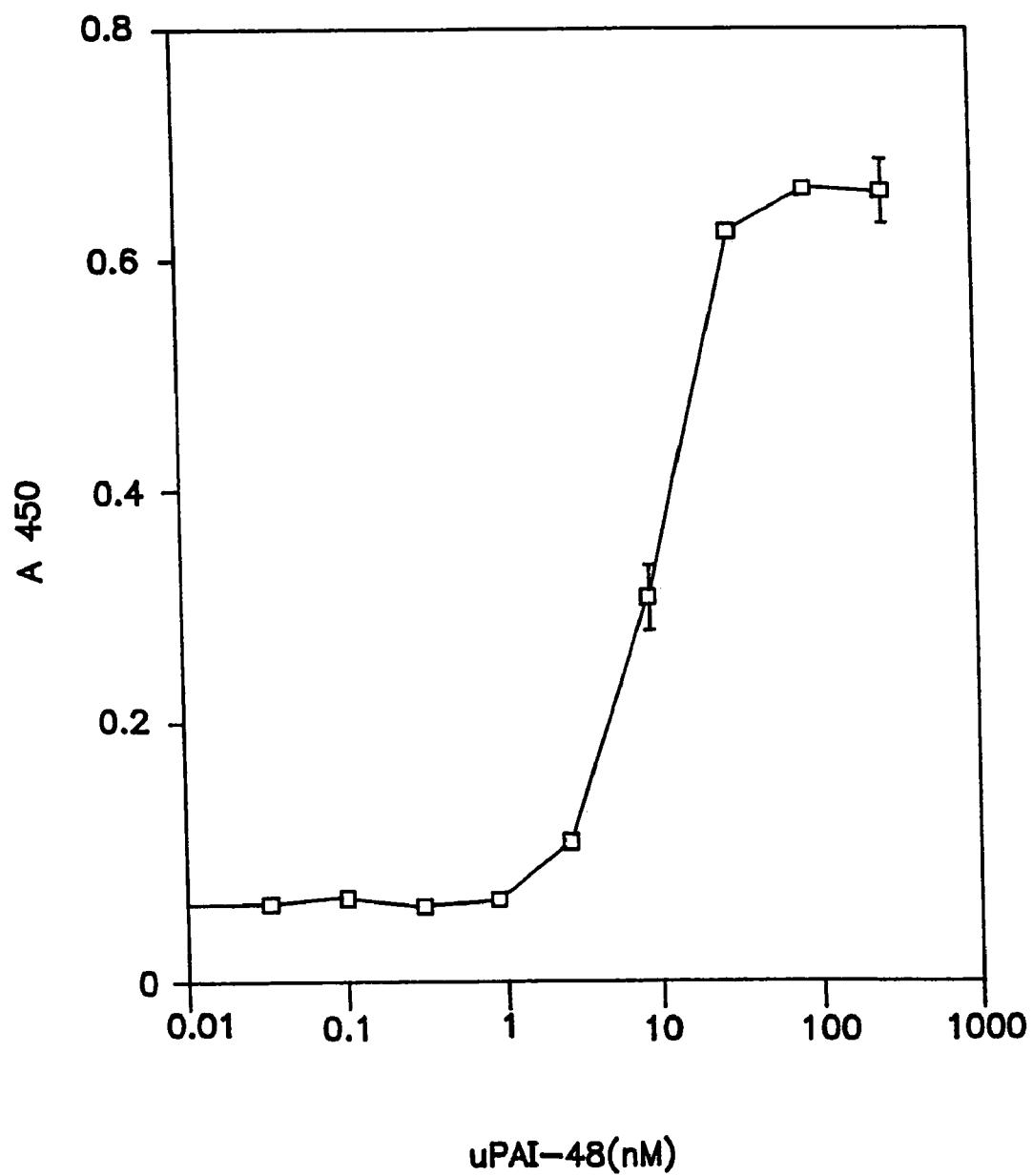
Figure 2:
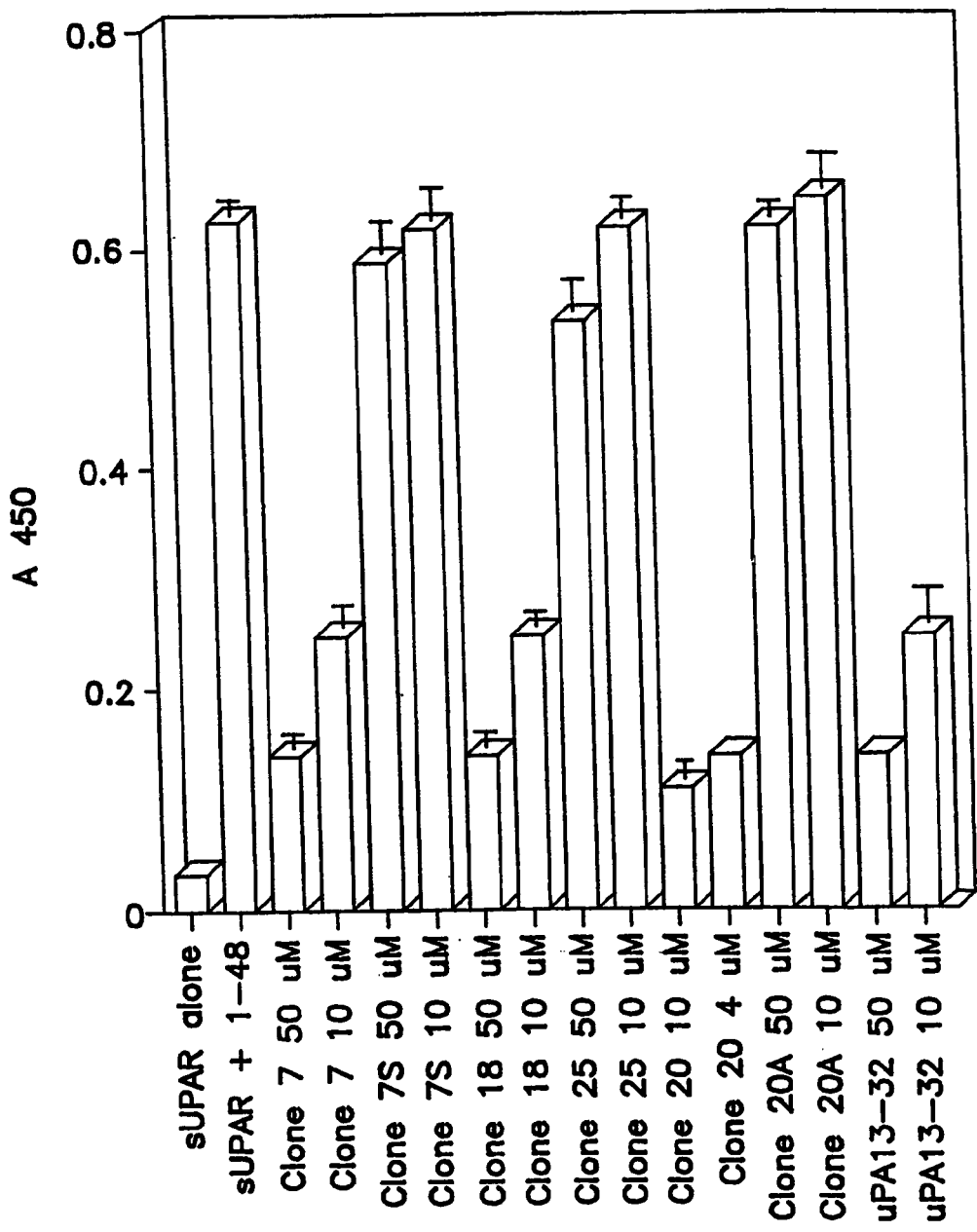

| Clone | Sequence | Phage Yield[1] | | IC 50 (uM)[2] | |
|---|---|---|---|---|---|
| | | −1−48 | +1−48 | −1−48 | +1−48 |
| 7 | AE PVYQYELDSYLRSYY | 4.1 | 4.1 | 10 | |
| 9 | AE FFKLGPNGYVYLHSA | 5.4 | 3.6 | NT[3] | |
| 18 | AE LDLSTFYDIQYLLRT | 2.6 | 1.2 | 10 | |
| 25 | AE STYHHLSLGYMYTLN | 4.9 | 2.1 | >10 | |
| 20[4] | AE PMPHSLNFSQYLWYT | 2.6 | .003 | 0.01 | |
| 13−32[4] | CLNGGTAVSNKYFSNLHWC | 2.1 | .001 | 0.25 | |

FIG. 6

PEPTIDE LIGANDS OF THE UROKINASE RECEPTOR

CROSS REFERENCE TO RELATED APPLICATIONS

This application is a divisional of prior application Ser. No.: 09/155,260, filed on Sep. 23, 1998, now U.S. Pat. No. 6,794,358 entitled, "PEPTIDE LIGANDS OF THE UROKINASE RECEPTOR" by Steven Rosenberg, Michael V. Doyle, and Harold A. Chapman, which further claims priority to PCT/US97/05199, filed Mar. 28, 1997, entitled, "PEPTIDE LIGANDS OF THE UROKINASE RECEPTOR" by Steven Rosenberg, Michael V. Doyle, and Harold A. Chapman.

FIELD OF THE INVENTION

This invention relates to the identification of novel functional sites on the urokinase receptor in the presence of the receptor binding region of urokinase. Described herein are peptides derived from bacteriophage display that identify the sites, and a general method for identifying functional sites on proteins using bacteriophage display. Also, methods of using urokinase receptor functional sites for studies of vitronectin and integrin interaction with urokinase:urokinase receptor complex interaction are described. Also described are uses of the instant peptides for developing therapeutic molecules capable of antagonisting interactions of the vitronectin and integrin peptides with the urokinase:urokinase receptor complex.

BACKGROUND OF THE INVENTION

The urokinase plasminogen activator (uPA) is a serine protease that interacts with its cell surface receptor (uPAR) providing an inducible, localized cell surface proteolytic activity, thereby promoting cellular invasion. The uPA:uPAR complex converts plasminogen into plasmin which is known to degrade various matrix glycoproteins as described in Ellis et al, *J. Biol. Chem.* 264: 2185–2188 (1989), Vassili et al, *J. Clin. Invest.* 88: 1067–1072 (1991), and Mignatti and Rifkin, *Physiol. Rev.* 73: 161–195 (1993). The simaltaneous expression of uPA and its receptor has been associated with localized plasminogen activation and pericellular matrix degradation during directed cell migration of normal and tumor cells.

The urokinase receptor (uPAR) is a 283 amino acid glycosylphosphatidyl-inositol (GPI)—anchored receptor protein of urokinase and vitronectin which appears to be a triplication of a 90 amino acid domain as described in Plough, and Ellis, *FEBS Lett.* 349:163–168 (1994) and Roldan et al, *EMBO J.* 9: 467–474 (1990). Proteolysis of uPAR can yield fragments composed of domain 1 and domains 2–3, and subsequent analysis has shown that disulfide bonding pattern of domain 1 is completely internal to the domain, as described in Plough et al, *J. Biol. Chem.* 268:17539–17546 (1993), and Kieffer et al, *Biochem.* 33:4471–4482 (1994).

The migration and invasion of cells appear to require cell surface localized proteolysis and adhesion to specific components of the extracellular matrix. These processes are necessary for many normal and pathological processes, including tissue remodeling, embryo implantation, angiogenesis, and tumor cell invasion and metastasis as described in Fazioli et al, *Trends Pharimacol. Sci.* 15:25–29(1994), and Mignatti et al, *Physiol. Rev.* 73:161–195 (1993). Important components of the cell surface proteolytic and cellular adhesion cascades are the plasminogen activator/plasmin system, matrix metalloproteinases, and integrins, as described in Felding-Habermann et al, *Curr. Biol.* 5 864–868 (1993). Adhesion to the extracellular matrix component vitronectin has been reported to correlate with UPAR expression, and uPA binding sites and vitronectin receptors have been shown to colocalize on HT1080 cells, as described in Waltz et al, *J. Biol. Chem.* 269: 14746–14750 (1994), and Ciambrone et al, *J. Biol. Chem.* 267: 13617–13622 (1992). More recently it has been demonstrated that uPAR can function as a cell adhesion receptor for vitronectin in a uPA dependent manner as described in Wei et al, *J. Biol. Chem.* 269: 32380–32388 (1994).

Early experiments using chemical cross-linking suggested that the first domain of uPAR was sufficient for high affinity binding of uPA, however, subsequent work has shown that an intact 3-domain molecule is required, and that additional binding determinants in domains 2 and 3 are likely involved, as described in Plough et al, *Biochem.* 3: 8991–8997 (1994). The undefined interactions may be with the uPA EGF-like domain or indirect interactions affecting the conformation of domain 1. Previous work has been unsuccessful in distinguishing whether domain 2 and 3 has measurable affinity for uPA, because of the difficulty of separating domain 2 and 3 from trace amounts of full length uPAR as described in Plough et al, *Biochem.* 3: 8991–8997 (1994).

The uPA:uPAR system has been identified as promoting pericellular proteolysis, and functions attributable to uPAR include cell migration, adhesion and mitogenesis. It would be desirable, therefore, to elucidate the function of domains 2 and 3 of uPAR.

SUMMARY OF THE INVENTION

A first embodiment of the invention is a method of identifying an orphan binding site on a target polypeptide sequence by
  (a) providing
    (1) a library of potential ligands,
    (2) a target polypeptide in contact with a known ligand for the target polypeptide,
  (b) contacting the target polypeptide and known ligand with the library of potential ligands, and
  (c) identifying the potential ligand that binds to the target polypeptide in the presence of the known ligand to form a binding pair with the target polypeptide and known ligand.

Another embodiment of the invention is an isolated peptide that binds a urokinase plasminogen activator receptor (uPAR) and inhibits uPAR binding to an integrin. The isolated peptide can be YHXLXXYMYT (SEQU ID NO:5) or AESTYHHLSLGYMYTLN (SEQ ID NO:4).

Another embodiment of the invention is an isolated peptide that binds a urokinase plasminogen activator (uPAR) and inhibits uPAR binding to vitronectin. The isolated peptide can be AEPVYQYELDSYLRSYY (SEQ ID NO: 1), AEFFKLGPNGYVYLHSA (SEQ ID NO:2), or AELDLSTFYDIQYLLRT (SEQ ID NO:3) or FKLXXXGYVYL (SEQ ID NO:6).

Yet another embodiment of the invention is an isolated nucleic acid sequence that encodes a peptide that binds a urokinase plasminogen activator receptor (uPAR) and inhibits uPAR binding to an integrin. The isolated nucleic acid sequence can encode the amino acid sequence of YHXLXXYMYT (SEQ ID NO:5) or STYHHLSLGYMYTLN (SEQ ID NO:4).

Still another embodiment of the invention is an isolated nucleic acid sequence that encodes a peptide that binds a urokinase plasminogen activator receptor (uPAR) and inhibits uPAR binding to vitronectin. The isolated nucleic acid sequence can encode the amino acid sequence of AEPVYQYELDSYLRSYY (SEQ ID NO:1), or FFKLGPNGYVYLHSA (SEQ ID NO:2) or, AELDLSIFYDIQYLLRT (SEQ ID NO:3) or FKLXXXGYVYL (SEQ ID NO:6).

Yet another embodiment of the invention is a method of treating a patient with a disorder characterized by upregulation of uPA and uPAR by providing an effective amount of an antagonist of a uPAR:integrin binding pair, and administering the antagonist to the patient.

An additional embodiment of the invention is a method of screening for an antagonist of uPAR:integrin interaction comprising the steps of providing a peptide antagonist of a uPAR:integrin interaction, competing the peptide antagonist with a candidate antagonist for binding to uPAR, and identifying a candidate antagonist by the ability to compete with the peptide antagonist for uPAR binding.

Still a further embodiment of the invention is a small molecule antagonist of a uPAR:integrin interaction identified by the just described method; a peptide antagonist of a uPAR:integrin interaction identified by that method; and a peptoid antagonist of a uPAR:integrin interaction identified by the same method.

Another embodiment of the invention is a pharmaceutical composition for treating a disorder characterized by upregulation of uPA and uPAR comprising an effective amount of an antagonist of a uPAR:integrin binding pair and a pharmaceutically acceptable carrier.

Yet another embodiment of the invention is a pharmaceutical composition for treating a patient with a disorder characterized by upregulation of uPA and uPAR comprising an effective amount of a nucleic acid encoding a peptide antagonist of a uPAR:integrin binding pair and a pharmaceutically acceptable carrier suitable for expressing the peptide in the patient.

BRIEF DESCRIPTION OF THE DRAWINGS

FIG. 1. UPA1–48 is required for sUPAR binding to vitronectin. Various concentrations of uPA1–48 were incubated with biotinylated sUPAR in vitronectin-coated wells and vitronectin-bound sUPAR detected as described in the examples. Each determination was in duplicate and the results are reported as the mean absorbance at 450 nm of the sUPAR plus uPA1–48 samples minus the mean absorbance of the sUPAR alone sample (approximately 0.03).

FIG. 2. Effects of various peptide ligands on sUPAR binding to vitronectin. The effects of the indicated peptides on sUPAR/vitronectin interaction were determined by incubating the peptides with biotinylated sUPAR in vitronectin-coated wells in the presence of uPA1–48 as in FIG. 1. All peptides were solubilized in 100% DMSO before diluting to the indicated concentrations with PBS/2% BSA for the assay. Control samples included suPAR plus 20 nM UPA1–48 and sUPAR alone. Peptides tested were clone 7, clone 7S (scrambled clone 7), clone 18, clone 25, clone 20, clone 20A (L to A replacement at position 14), and uPA 13–32 C19A. Results are reported as the mean $OD_{450}$ values of triplicate points. Where error bars are not shown they are smaller than the symbols.

FIG 3. Peptides 7 and 18 are Homologous to the Somatomedin B Domain of Vitronectin. The sequence of vitronectin (SEQ ID No:9) from residues 1–47 including the somatomedin B domain and RGD motif is compared with the sequences of clones 7 (SEQ ID NO:10) and 18 (SEQ ID NO:11). Homologous residues at positions 22–28 in vitronectin and in the bacteriophage derived peptides are in bold as in the RGD sequence in vitronectin.

FIG 4. Alanine Replacement of Peptide 7 Affects Both Bacteriophage and Vitronectin Binding to UPAR. Synthetic peptides at 40 μm were tested as competitors for binding of bacteriophage 7 (portion of SEQ ID NO:10) to biotinylated suPAR as described in Materials and Methods and shown in panel A. Bacteriophage were detected with a rabbit anti-M13 antibody as described. The indicated values are the mean of triplicate determinations. The same peptides were tested in triplicate at 50 μm in the uPA1–48:uPAR:vitronectin binding ELISA.

FIG. 5. Bacteriophage binding to sUPAR domain 2/3. Phage were added to wells containing sUPAR domain 2/3 immobilized by its epitope tag via protein G and monoclonal antibody to the epitope tag. Wells containing protein G and antibody but no domain 2/3 were included to determine nonspecific phage binding. Urea-eluted phage and the input stocks were titered by plaque formation assay. Results were single point determinations calculated as a percent of the input titer and were repeated in three separate experiments.

FIG 6: Table. The table of FIG 6 depicts the sequences (SEQ ID NOS:12–17), phage yields, and IC50s in uPAR binding assays for selected phage peptides. Legend: 1. Individual phage were incubated with biotinylated suPAR with and without 10 μM uPA1–48 on streptavidin coated wells as described herein. The background yields of all phage without SuPAR in the wells ranged from 0.002–0.025%. Errors in yield are in the range 50%. 2. Apparent inhibition constant of the synthetic peptide in the uPAR receptor binding assay; errors are in the range of 20%. 3. NT=not determined because of peptide insolubility. 4. Clone 20 and 13–32 peptides were as described previously.

DETAILED DESCRIPTION OF THE PREFERRED EMBODIMENTS

The invention described herein draws on previously published work and pending patent applications. By way of example, such work consists of scientific papers, patents or pending patent applications. All such published work cited herein are hereby incorporated by reference. The invention can be better understood in light of the following definitions incorporated herein.

Definitions

The term "orphan binding site" as used herein refers to a previously unidentified site on a polypeptide sequence that is capable of binding to another peptide or polypeptide sequence. The orphan binding site is distinguishable from a binding site for which the native ligand is known. The orphan binding sites of the invention are discovered by phage display of a peptide sequence that is capable of binding a site on a target polypeptide. The binding site may involve binding of a third or fourth additional polypeptide, for example, where the urokinase plasminogen activator receptor (uPAR) binds urokinase plasminogen activator (uPA) in addition to binding other ligands or polypeptides, such as, for example vitronectin and integrin.

The term "orphan polypeptide" as used herein refers to a polypeptide sequence capable of binding at an orphan binding site. The orphan polypeptide may be, for example, a peptide used in a phage display screening to determine orphan binding sites, or may be the polypeptide sequence of a native or synthetic molecule that binds the orphan binding site, and is homologous in sequence to the peptide used to determine the location of the orphan binding site.

The term "potential ligand" as used herein refers to any peptide, polynucleotide, polysaccharide, or other molecule that could potentially bind to the target polypeptide.

The term "potential ligand library" as used herein refers to a collection or mixture of at least 50 compounds that are potential ligands as defined above, and more preferably a potential ligand library is at least 200 potential ligand compounds, and still more preferably more than 500 compounds.

The term "unknown ligand" as used herein refers to ligands of a target polypeptide that have not yet been discovered, but that may be discovered by the method of the invention. Where a potential ligand can bind a target polypeptide, and antagonize binding of a previously unknown ligand, the identity and existence of the unknown ligand can be determined either by structural analysis of the potential ligand that binds a target polypeptide, or by functional changes that indicate that binding has been disrupted by an antagonist. The unknown ligand can also be determined by screening a library of polypeptides comprising sequences that occur naturally in a competition assay with the potential ligand bound to the target polypeptide at the orphan binding site.

The term "bacteriophage library" as used herein refers to the technique in molecular biology of creating a library of peptides expressed on the surface of a bacteriophage for presentation and contacting potential target polypeptides. The library is the polynucleotides that are expressable as peptides and presented by the bacteriophage, and may be the DNA or the amino acid moieties used or generated by this technique. Bacteriophage panning or display has applications as described herein for screening for ligands of target polypeptides, which when identified, also identifies orphan binding sites on the target polypeptides.

The term "peptide" and the term "polypeptide" as used herein refers to a peptide or a polypeptide produced in vivo or in vitro in an environment manipulated by humans using techniques of molecular biology, biochemistry or gene therapy. For example, an isolated peptide or polypeptide can be produced in a cell free system by automated peptide or polypeptide synthesis, in heterologous host cells transformed with the nucleic acid sequence encoding the peptide or polypeptide and regulatory sequences for expression in the host cells, and in an animal into which the coding sequence of the peptide or polypeptide has been introduced for expression in the animal. A peptide or polypeptide isolated for purposes herein to the extent that it is not present in its natural. state inside a cell as a product of nature. For example, such isolated polypeptides or polynucleotides can be 10% pure, 20% pure, or a higher degree of purity.

The term "derivative" as used herein in reference to a peptide, polypeptide or a polynucleotide means a peptide, polypeptide or polynucleotide that retains the functionality of the peptide, polypeptide or polynucleotide to which it is a derivative. They may be variously modified by amino acid deletions, substitutions, insertions or inversions by, for example, site directed mutagenesis of the underlying nucleic acid molecules. Derivatives of a peptide, polypeptide or polynucleotide may also be fragments thereof. In any case, a derivative, or a fragment, retains at least some, and preferably all of the function of the peptide or polypeptide from which it is derived.

The term "pharmaceutical composition" refers to a composition for administration of a therapeutic agent. The therapeutic agent can be, for example a peptide, a polypeptide, a polynucleotide, a small molecule, a peptoid, or a derivative of any of these, and refers to any pharmaceutical carrier that does not itself induce the production of antibodies harmful to the individual receiving the composition, and which may be administered without undue toxicity.

Administration of a therapeutic agent of the invention includes administration of a therapeutically effective amount of the agent of the invention. The term "therapeutically effective amount" as used herein refers to an amount of a therapeutic agent sufficient to treat or prevent a condition treatable by administration of a composition of the invention. That amount is the amount sufficient to exhibit a detectable therapeutic, preventitive or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance. However, the effective amount for a given situation can be determined by routine experimentation. Administration can include admininistration of a polypeptide, and causing the polypeptide to be expressed in an animal by administration of a polynucleotide encoding the polypeptide.

A "recombinant vector" herein refers to any vector for transfer or expression of the polynucleotides herein in a cell, including, for example, viral vectors, non-viral vectors, plasmid vectors and vectors derived from the regulatory sequences of heterologous hosts and expression systems.

A "regulatory sequence" herein refers to a nucleic acid sequence encoding one or more elements that are capable of affecting or effecting expression of a gene sequence, including transcription or translation thereof, when the gene sequence is placed in such a position as to subject it to the control thereof. Such a regulatory sequence can be, for example, a minimal promoter sequence, a complete promoter sequence, an induced active promoter, an enhancer sequence, an upstream activation sequence ("UAS"), an operator sequence, a downstream termination sequence, a polyadenylation sequence, an optimal 5' leader sequence to optimize initiation of translation, or a Shine-Dalgarno sequence. Alternatively, the regulatory sequence can contain a hybrid of promoters of any of the above, such as a hybrid enhancer/promoter element. The regulatory sequence that is appropriate for expression of the gene of interest differs depending upon the host system in which the construct is to be expressed. Selection of the appropriate regulatory sequences for use herein is within the capability of one skilled in the art. In eukaryotes, for example, such a sequence can include one or more of a promoter sequence and/or a transcription termination sequence. Regulatory sequences suitable for use herein may be derived from any source including a prokaryotic source, an eukaryotic source, a virus, a viral vector, a bacteriophage or a linear or circular plasmid. The regulatory sequence herein can also be a synthetic sequence, for example, one made by combining the UAS of one gene with the remainder of a requisite promoter from another gene, such as the GADP/ADH2 hybrid promoter. A regulatory sequence can also be a repressor sequence.

"Mammalian cell" as used herein refers to a subset of eukaryotic cells useful in the invention as host cells, and includes human cells, and animal cells such as those from dogs, cats, cattle, horses, rabbits, mice, goats, pigs, etc. The cells used can be genetically unaltered or can be genetically altered, for example, by transformation with appropriate expression vectors, marker genes, and the like. Mammalian cells suitable for the method of the invention are any mammalian cell capable of expressing the genes of interest, or any mammalian cells that can express a cDNA library, cRNA library, genomic DNA library or any protein or polypeptide useful in the method of the invention. Mammalian cells also include cells from cell lines such as those immortalized cell lines available from the American Type Culture Collection (ATCC). Such cell lines include, for example, rat pheochromocytoma cells (PC12 cells), embryonal carcinoma cells (P19 cells), Chinese hamster ovary (CHO) cells, HeLa cells, baby hamster kidney (BHK) cells, monkey kidney cells (COS), human hepatoceflular carcinoma cells (e.g., Hep G2), human embryonic kidney cells, mouse sertoli cells, canine kidney cells, buffalo rat liver cells, human lung cells, human liver cells, mouse mammary tumor cells, as well as others. Also included are hematopoetic stem cells, neuronal stem cells such as neuronal sphere cells, and embryonic stem cells (ES cells).

A "polynucleotide sequence," a "nucleic acid molecule," a "nucleic acid sequence," or a "coding sequence," as used herein, refers to either RNA or DNA that encodes a specific amino acid sequence or its complementary strand. A nucleic acid molecule may also be an oligonucleotide probe that may or may not encode a functional peptide, for example, an antisense oligonucleotide sequence, or a ribozyme.

The term "analog" as used herein refers to splice variants, truncations, variants, alleles and derivatives and the like, of a mature protein. Unless specifically mentioned otherwise, the "analogs" possess one or more of the bioactivities of the "mature protein," or possess the bioactivity of the peptide. Thus, peptides or polypeptides that are identical or contain at least 60%, preferably 70%, more preferably 80%, and most preferably 90% amino acid sequence homology to the amino acid sequence of the mature protein or the peptide wherever derived, from human or nonhuman sources, are included within this definition.

The "variants" herein contain amino acid substitutions, deletions, or insertions. The amino acid substitutions can be conservative amino acid substitutions or substitutions to eliminate non-essential amino acid residues such as to alter a glycosylation site, a phosphorylation site, an acetylation site, or to minimize misfolding by substitution or deletion of one or more cysteine residues that are not necessary for function. Conservative amino acid substitutions are those that preserve the general charge, hydiophobicity/hydrophilicity and/or steric bulk of the amino acid substituted, for example, substitutions between the members of the following groups are conservative substitutions: Gly/Ala, Val/Ile/Leu, Asp/Glu, Lys/Arg, Asn/Gln, Ser/Thr/Cys and Phe/Trp/Tyr. The analogs herein further include peptides having one or more peptide mimics, also known as peptoids, that possess the bioactivity of the protein. Included within the definition are also polypeptides containing one or more analog amino acid (including, for example, unnatural amino acids, etc.), polypeptides with substituted linkages, as well as other modifications known in the art, both naturally occurring and non-naturally occurring. The term polypeptide also does not exclude post-expression modifications of the polypeptide, for example, glycosylations, acetylations, phosphorylations and the like.

The term "binding pair" refers to a pair of molecules, usually referring to a protein/protein pair, but does not exclude a protein/DNA pair, or a protein/RNA pair, or DNA/DNA pair, DNA/RNA pair or RNA/RNA pair, and can include small molecules that bind protein or DNA or RNA. The components of such pair bind specifically to each other with a higher affinity than to a random molecule, such that upon binding, for example, in case of a ligand/receptor interaction, the binding pair triggers a cellular or an intracellular response, or forms a complex. An example of a ligand/receptor binding pair is a pair formed between PDGF (platelet derived growth factor) and a PDGF receptor. An example of a different binding pair is an antigen/antibody pair in which the antibody is generated by immunization of a host with the antigen. An example of an organic molecule—protein binding pair is the binding of retinoic acid with its protein receptor, the retinoic acid receptor. Specific binding indicates a binding interaction having a low dissociation constant, which distinguishes specific binding from non-specific, background, binding. A low dissociation constant would be, for example, 1.0 µM, more preferably 10 nM, still more preferably 1.0 nM or less.

The term "antagonist" as used herein refers to a molecule that blocks signalling to a detectable degree, as for example, a molecule that can bind a receptor, but which does not cause a signal to be transduced by the receptor to the cell. In the case of an antagonist peptide, the peptide antagonist can bind, for example, the uPAR receptor at or near the integrin binding site, and prevent integrin from forming a binding pair with uPAR.

The term "agonist" as used herein refers to a molecule that mimics the signalling in the pathway under study, for example, by binding a receptor and promoting a signal transduction to the cell through the receptor. In the case of the invention, an agonist of a peptide antagonist of uPAR would mimic or be able to compete with the peptide antagonist for blocking the formation of a uPAR:integrin binding pair. Small molecules or peptoids can be screened for the ability to perform the same or similar function of a peptide antagonist of the uPAR:integrin binding pair interaction.

The urokinase plasminogen activator receptor "uPAR" as used herein refers to the urokinase plasminogen activator receptor. uPAR is a glycosylphosphatidyl-inositol-linked urokinase and vitronectin receptor. uPAR is expressed on many cells as a consequence of cytokine stimulation or malignant transformation as described in Blasi et al, *J. Cell. Biol.* 104: 801(1987).

Urokinase plasminogen activator "uPA" as used herein refers to a serine protease capable of activating urokinase plasminogen. When bound to its cell surface receptor, uPAR, uPA converts plasminogen to plasmin.

"Integrin" as used herein refers to the integrin farily of cell adhesion receptors known to mediate cell attachment to extracellular matrix proteins and also known to play a critical role in cell motility.

The term "cytoskeletal disorder" as used herein refers to a disorder in a patient that can be characterized at least in part by the formation of an abnormal condition in the cytoskeleton of at least one tissue of the patient. Cytoskeletal abnormalities can be associated with a variety of conditions, including, for example, tumor growth, metastatic cancer, angiogenesis, wounds, and other disorders.

Some of the abbreviations used herein are: EGF, epidermal growth factor; uPA, urokinase plasminogen activator, uPA1–48, amino acids 1 to 48 of urokinase; uPAR, urokinase plasminogen activator receptor; sUPAR, soluble truncated form of the urokinase receptor; uPA13–32, amino acids 13–32 of human urokinase with Cys19 converted to Ala; PAI-1, plasminogen activator inhibitor type-1; ATF, amino terminal fragment of uPA; HRP, horse radish peroxidase; PBS, phosphate buffered saline; BSA, bovine serum albumin.

The invention is the use of bacteriophage display to identify novel functional sites on proteins. Using this novel application of bacteriophage display techniques, the inventors have identified novel peptide sequences that bind to the human urokinase receptor in the presence of the receptor binding region of human urokinase, and so identified novel functional sites.

Accordingly, the identified peptides define two new functional sites on the urokinase receptor. The first is a site that corresponds to the interaction site of urokinase:urokinase receptor complexes with vitronectin and show homology to the somatomedin B domain of vitronectin. The second functional site is involved in a previously unexpected interaction of the urokinase receptor with integrins and likely defines the integrin:urokinase receptor interface. Modulation of this second site can lead to alterations in integrin activity/specificity and affect cell adhesion and other integrin mediated events.

The invention includes three peptides that inhibit the uPAR:vitronectin binding interaction, peptide 7 (SEQ ID NO:1), peptide 9 (SEQ ID NO:2), and peptide 18 (SEQ ID NO:3), and use of these peptides to inhibit the uPAR: vitronectin interaction. Vitronectin has been implicated in binding to uPAR as described in Waltz et al, *J. Biol. Chem.* 269: 14746–14750 (1994). It has been shown that the urokinase receptor can be a uPA dependent adhesion receptor for vitronectin as described in Wei et al, *J. Biol. Chem.* 269:32380–32388 (1994). Vitronectin is a complex glycoprotein with a modular domain structure which exists in both circulating and extracellular matrix forms as described in Preissner et al, *Annu. Rev. Cell Biol.* 7: 275–310(1991). It interacts with a variety of cell surface components, including integrins with the alpha-v subunit as described in Felding-Habrann et al, *Curr. Biol.* 5,864–868. (1993), as well as with the active conformation of PAI-1 as described in Mimuro et al, *J. Biol. Chem.* 264: 936–939 (1989). This latter interacton appears to be via the somatomedin B domain of vitronectin as described in Seiffert et al, *J. Biol. Chem.* 266: 2824–2830(1991), and Seiffert et al, *J. Biol. Chem.* 269: 2659–2666 (1984). More recently it has been shown that vitronectin colocalizes with uPA in the extracular matrix at focal contacts as described in Ciambrone et al, *J. Biol. Chem.* 267: 13617–13622 (1992). An explanation of this phenomenon was provided by the demonstration that uPAR is an adhesion receptor for vitronectin, whose binding is stimulated by uPA as described in Wei et al, *J. Biol. Chem.* 269: 32380–32388 (1994).

We have discovered 15 mer peptides from bacteriophage display that inhibit the binding of uPA1–48:uPAR complexes to vitronectin in vitro ad tht block the adhesion of U937 cells to vitronectin. These peptides show homology with the somatomedin B domain of vitronectin. The homology suggests that the binding sites of uPAR:uPA1–48 complexes and PAI-1 may overlap, which is shown by the fact that PAI-1 competes for binding of these complexes to vitronectin. The putative alignment of the bacteriophage derived peptides and vitronectin sequence suggests that binding of uPAR:uPA1–48 complexes occurs close to the binding site of $a_v$ integrins, as defined by the RGD sequence found at residues 45–47, only 16 amino acids away from the C-terminus of the uPAR binding site. The proximity of these binding sites in vitronectin suggests the possibility of cooperative interactions between uPAR and integrins. Such an interaction might provide a mechanism for the signalling capability of uPAR via functional coupling with integrin vitronectin receptors, where vitronectin serves to cross-link uPAR and the integrin. This would provide an explanation for how a GPI-linked integral membrane protein transmits signals to the cell.

The invention also includes specific peptides that represent examples of a uPAR:integrin site, such as peptide 25 (SEQ ID NO:4). Clone 25 represents a distinct sequence motif, and based on the equivalent binding to D 23, identify a unique binding sufficient for inhibiting the binding pair interaction between uPAR and integrin is GYZY, where Z is M or V. Peptide 25 has been shown to bind to the urokinase receptor and modulates integrin function. The sequence of peptide 25 is (SEQ ID NO:15) AESTYHHLSLGYMYTLN, where, by alanine replacement the amino acids (SEQ ID NO:5) YHXLXXGYMYT, where X is any amino acid were determined to be important for inhibiting uPAR binding to integrin.

A further aspect of the invention is the use of peptide 25 as a lead compound and a tool for assay development of other molecules with the same activity, for example, small molecules and peptoids.

Other workers have shown that uPAR and both $b_2$ integrins, specifically Mac-1, and $a_vb_3$ and $a_vb_5$ appear to colocalize in cells as described in Xue et al. *J. Immunol.* 152: 4630–4640 (1994), Bohuslav et al, *J. Exp. Med.* 181: 1381–1390 (1995), Conforti et al, *Blood* 83: 994–1005 (1994), and Reinartz et al, *Exp. Cell Res.* 220: 271–282 (1995). However, in none of these cases was there a direct probe for looking at the potential biochemical interaction between uPAR and the integrins.

Previous work had demonstrated that selection of high affinity peptide ligands for the uPA binding site on uPAR was a relatively efficient process, as described in Goodson et al, *Proc. Natl. Acad. Sci. USA* 91: 7129–7133 (1994). We extended this analysis by selecting for peptide-displaying bacteriophage with affinity for additional, functionally important sites on uPAR by including an excess of recombinant EGF-like domain of uPA (uPA1–48) to reduce selection of uPA binding site peptides, as described in Stratton-Thomas et al. *Prot. Eng.* 8: 463470 (1995). The EGF-like domain is the receptor binding motif and binds to uPAR with similar affinity (0.1–5 nM) as uPA. The 15 mer random peptide bacteriophage library, as described in Devlin et al, *Science* 249: 404–406 (1990) was affinity selected on suPAR:uPA1–48 complexes immobilized on magnetic beads.

In order to analyze the effects of the various peptide ligands on the uPAR:vitronectin interaction, we developed an in vitro ELISA based assay for this interaction. Under the conditions of the assay binding of biotinylated uPAR to vitronectin is strictly dependent on uPA1–48, as shown in FIG. 1. The apparently stoichiometric binding of the uPA1–48:suPAR complexes to vitronectin indicates that the affinity of this interaction is higher than the concentration of complex (Kd<20 nM).

The ability of the various bacteriophage derived peptides to affect binding of uPA1–48:uPAR complexes to vitronectin was then assessed in the ELISA assay. Two classes of peptides were effective antagonists in this assay. First, clone 20 and uPA13–32, which compete directly for uPA1–48 binding to sUPAR, reduce binding. An analog of clone 20 peptide, which shows greatly reduced receptor binding activity, did not affect binding to vitronectin. Second, clones 7 and 18, which show greatly reduced competition for uPA1–48 binding (see table in FIG. 6) also inhibit complex binding, while a scrambled version of clone 7 (having the same amino acids as clone 7, but in a different order) does not. None of the peptides when tested alone increased the binding of biotinylated sUPAR to vitronectin.

A third peptide, clone 25, bound efficiently to suPAk as a bacteriophage, had little or no effect on uPA1–48 stimulated vitronectin binding.

In order to test whether the clone 7 and 18 peptides bound directly at the vitronectin binding site on uPAR, and inhibited vitronectin binding by uPAR:uPA1–18 by direct competition for that site, the inventors examined the effects of vitronectin on the binding of these bacteriophage. Vitronectin reduced bacteriophage binding to the uPA1–48: suPAR complex by 5–10 fold, consistent with the hypothesis that these peptides mirnic vitronectin as a uPAR ligand.

Previous results had shown that vitronectin binding by uPAR correlated with cell adhesion of stimulated U937 cells as described in Wei etal, *J. Biol. Chem.* 269: 32380–32388 (1994). Whether clone 7 peptide could block uPAR mediated adhesion of these cells was then tested, with the result that clone 7 is an effective blocker of uPAR:vitronectin interaction, whereas a scrambled version of the same peptide showed no effect.

We demonstrated that binding of uPA1–48:uPAR complexes to vitronectin is blocked by PAI-1, vitronectin, and the somatomedin B domain of vitronectin. Another function of vitronectin is to stabilize the active conformation of PAI-1, which appears to occur via the somatomedin B domain of vitronectin as described in Seiffert et al, *J. Biol. Clzem.* 269: 2659–2666 (1994). PAI-1 is a very efficient competitor of uPA1–48:suPAR complexes binding to vitronectin, with an apparent IC50 of 10 nM. This suggested that the binding site of uPAR and PAI-1 are overlapping. It has been demonstrated as described in Seiffert et al, *J. Biol. Chem.* 269: 2659–2666 (1994) that high affinity vitronectin binding to active PAI-1 is primarily via the somatomedin B domain. The inventors tested whether vitronectin and recombinant somatomedin B domain would also inhibit uPAR binding to vitronectin, and found that both molecules inhibit, whereas a point mutation of the domain abolishes their inhibition.

Figure 4:
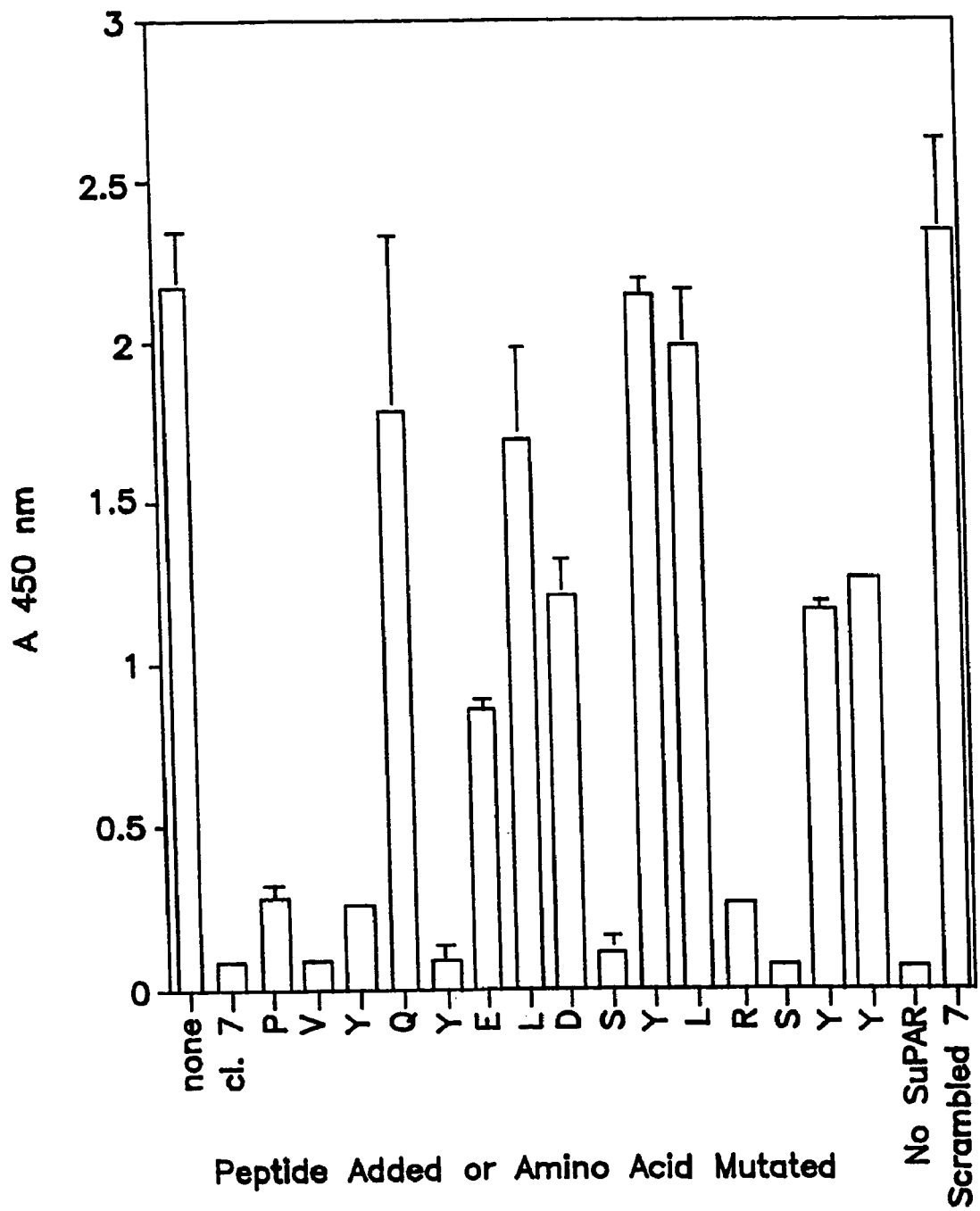

We identified bacteriophage peptides that are homologous to the somatomedin B domain of vitronectin, the binding site of PAI-1. The somatomedin B domain of vitronectin blocks uPAR binding, and accordingly we examined the sequences of bacteriophage derived peptides 7 and 18 for homology to this domain. As shown in FIG. 4, there is a conserved motif, LXXArY (where X is a hydrophilic residue, and Ar=F,Y) between residues 24–28 of the somatomedin B domain and clone 7 and 18 peptides. In addition, clones 7 and 18 share the sequence E-L-D just N-terminal to the conserved leucine, whereas the related sequence D-E-L is found in the somatomedin B domain of vitronectin at residues 22–24, adjacent to the conserved sequence LCSYY.

To determine which residues in peptide 7 are important for uPAR binding and inhibition of vitronectin binding, we replaced each residue separately with alanine, and tested the resulting peptides for inhibition of bacteriophage binding to uPAR, and blockade of the binding of uPA1–48:uPAR complexes to vitronectin. The results shown in FIG. 5, indicate that the residues conserved between the peptides and vitronectin are important for activity in these assays.

Further, we determined that recombinant uPAR domain2–3 fragment binds bacteriophage but not uPA1–48. uPAR is the only member of the Ly6/CD59 family to contain three repeats of the homologous cysteine containing domain Plough et al, *FEBS Lett.* 349: 163–168 (1994). Our previous work suggests that the binding site for vitronectin on uPAR is in domains 2 and 3 (D23) as described in Wei et al, *J. Biol. Chem.* 269: 32380–32388 (1994). To further address this question the inventors expressed in baculovirus infected Sf9 insect cells a fragment of suPAR, residues 93–313, predicted to encompass the second and third CD59 homologous domains with a C-terminal 6 amino acid epitope tag. The secreted protein was purified on an anti-epitope affinity column, and was tested first for its ability to compete in the suPAR binding assay. There was no competition in this assay at 100 nM D23, in contrast to intact suPAR which shows an IC50 of 0.1 nM under the same conditions.

The inventors then tested the ability of various uPAR bacteriophage displayed ligands to bind to immobilized D23. The results shown in FIG. 6, indicate that the ligands fall into three different classes with respect to binding to D23 and sUPAR. Clone 20 and 13–32 bind signficantly only to intact sUPAR, whereas clones 9 and 25 bind equivalently to the D23 fragment and full-length receptor. Bacteriophage bearing clones 7 and 18 peptides show an intermediate degree of binding to D23, and substantially better binding to an intact receptor.

Integrins are a class of heterodimeric receptors implicated in adhesive interactions that regulate cell trafficking and intracellular signalling events important to cellular differentiation, migration and survival as described in Dustin et al, *Nature* 329: 846 (1987) and Shattil et al, *Curr. Opin. Cell Biol.* 6: 695 (1994). Adhesion of cells via integrins requires, in addition to ligand binding, a reorganization of intregrin distribution and assembly of connecting elements that link integrins to the cytoskeleton as described in Miyamoto et al, *Science* 267:883 (1995) and Burridge et al, *Annu. Rev. Cell Biol.* 4: 487 (1988). β1 integrins have been extensively studied in this regard. The cytoplasmic tail of β1 chains binds talin and alpha-actinin, which themselves interact directly with actin as described in Otey et al, *J. Cell. Biol.* 111: 721 (1990), and Schaller et al, *J. Cell. Biol.* 130: 1181 (1988). Further, the assembly of such cytoskeletal connections is not strictly a consequence of cell surface expression, but frequently requires secondary cell signaling as described in Faull et al, J. Cell. Biol. 121: 155 (1993), Masumoto et al, J. Biol. Chem. 268: 228 (1993), and Burn et al, Proc. Nat'l. Acad. Sci. U.S.A. 85: 497 (1988). Before the experimental events that gave rise to the present invention, integrin-associated proteins which might mediate dynamic alterations in the functional state of integrins remained largely undefined.

We determined that expression of uPAR not only confers adhesiveness for vitronectin but markedly diminishes β1-dependent adhesion of embryonic kidney cells (293 cells) to fibronectin. The study was based on an observation that expression of uPAR in 293 cells altered their integrin-dependent fibronectin and collagen adhesiveness. A phage display peptide library was screened for uPAR-binding phages. A number of uPAR-binding peptides as described in Goodson et al, *Proc. Nat'l Acad. Sci. U.S.A.* 91: 7129 (1994). Peptide 25 and several controls was synthesized, purified, and screened for their effect on adhesion. Peptide 25, but not the controls was found to abrogate glycophosphatidyl-inositol (GPI) linked uPAR dependent adhesion of 293 cells to vitronectin with an $IC_{50}$ of about 60 µM. Peptide 25 but not the controls, largely disrupted the β1/caveolin/uPAR complexes at concentrations which blocked adhesion, about 100 µM. These observations indentify a previously unrecognized functional unit within the cell membrane that regulates cellular adhesiveness. This unit consists of a GPI-anchored receptor (uPAR), an integrin, and caveolin, and likely other proteins known to associate with the cytoplasmic faces of β1 integrins and caveolin, including cytoskeletal elements.

To explore whether uPAR binds to integrins, nontransfected 293 cells were allowed to adhere to fibronectin or collagen in the presence of recombinant soluble uPAR (suPAR). The results indicated that suPAR inhibited adhesion of fibronectin and collagen in a dose dependent manner, and the inhibitor effect was reversible with the addition of a 100 μM peptide 25, but not a control. It was concluded that uPAR interacts with integrins that are in an active conformation and in so doing markedly altered integrin function. It was also shown that peptide 25 (100 μM) abrogated the interaction between another integrin, Mac-1 and uPAR, in the U937 cell line.

Studies to determine the functional consequences of uPAR/integrin interactions on cellular migration were also conducted, with the result that altered cell migration was observed in the presence of uPAR by creating a loss of integrin-dependent adhesiveness. Loss of stable cellular adhesion has been linked to malignant transformation, tumor cell invasion, and metastasis in several experimental and clinical situations as described in Huttenlocher et al, *Cell Biol.* 7: 697 (1995), Burchill et al, *BioEssays* 16: 225 (1994), and Lukashev et al, *J. Biol. Chem.* 26: 18311 (1994).

The invention includes the development of reagents such as that prototyped by peptide 25 demonstrated to disupt uPAR/integrin associations and restore integrin function, or reagents comparable to soluble uPAR which impair integrin function, such as for example, antibodies to the site on integrin of uPAR:integrin binding, for use in modifying inflammation and tumor progression.

Figure 5:
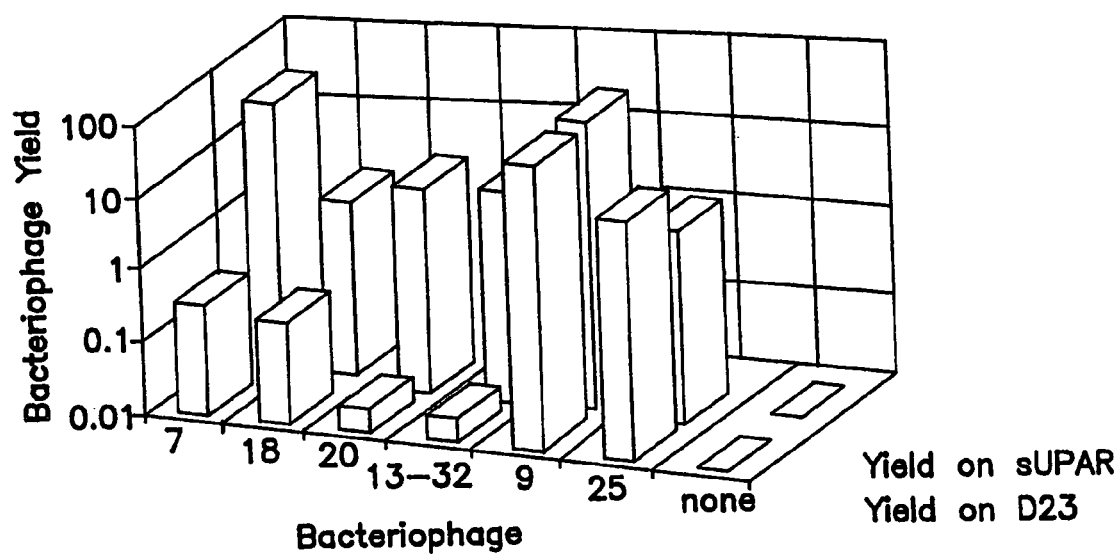

The sequences selected in this study which bind to suPAR, as represented by peptides 7 and 25, have distinct binding sites, based on several lines of evidence. First, these peptides show different effects on anilino-8-napthalene-sulfonate (ANS) fluorescence and as competitors for uPA1–48 binding as depicted in the table in FIG. 6. Second, only peptide 7 inhibits complex binding to vitronectin. Third, bacteriophage 25 shows equivalent binding to D23 and suPAR, whereas 7 shows about 50-fold reduced binding to D23. Peptide 18 appears to be of the same ligand family as 7, since it shows significant homology at the sequence level, and the conserved residues are important for clone 7 binding as indicated in FIG. 5. In particular, all of the defined residues in the motifs ELD and LxxArY are functionally important as judged by alanine replacement. In addition, peptide 18 blocks binding of complexes to vitronectin, as does peptide 7.

The invention also includes methods for screening for molecular mimics of the inhibitory activity of the peptides of the invention, for example peptide 7 and peptide 25, for the purpose of identifying, for example, small molecule or peptoid inhibitors of uPAR:vitronectin or uPAR:integrin binding interactions. Such antagonists of uPAR interactions can be, for example, peptide derivatives such as peptoids, small molecules, or polynucleotides. These antagonists are useful for development of therapeutics for treatment of conditions characterized by uPAR:vitronectin binding or by uPAR:integrin binding, or more generally, by upregulation of uPA and uPAR, where cell adhesion is compromised. The instant peptides and antagonist can be useful in treating a disease state or malady which is caused or exacerbated by the biological activity of uPA or uPAR. The conditions may also be characterized, for example, by cell migration and invasion, as seen in such disorders as, for example, tumor cell invasion, metastatic disease, and the condition may also be chronic inflammation.

Typically, the molecular mimics, peptoids or small molecules; or analogs, variants, or derivatives of the instant peptides exhibit a $K_d$ of less than 10 μM: more preferably, less than 5 μM, even more preferably less than 1 μM: even more preferably less than 100 nM; even more preferably less than 10 nM. with huPAR or the complex of huPAR:integrin or vitronectin.

Any of the full-length, derivatives, or polypeptide or peptide inhibitors or antagonists of the invention can be cloned, expressed, or synthesized by standard recombinant DNA or chemical techniques. Some exemplary expression systems that can be applied for these purposes follow. Administration of the peptide, polypeptide, and polynucleotide therapeutics of the invention can conducted by administration of the synthesizied peptide or polypeptide, or by administration of a polynucleotide for expression in an animal, or by administration of a non-coding polynucleotide inhibitor. Further below are also provided methods of making small molecule and peptoid library pools for screening for the desired activity. Also provided are gene therapy techniques for administering a polynucleotide of the invention to a patient for the purpose of expressing the polypeptide or peptide encoded by the polynucleotide or nucleic acid molecule in the animal. In addition, non-coding nucleic acid molecules, such as for example, ribozymes and antisense molecules can be administered with an appropriate pharmaceutically acceptable carrier.

Expression Systems

Although the methodology described below is believed to contain sufficient details to enable one skilled in the art to practice the present invention, other items not specifically exemplified, such as plasmids, can be constructed and purified using standard recombinant DNA techniques described in, for example, Sambrook et al. (1989), *MOLECULAR CLONING, A LABORATORY MANUAL*, 2d edition (Cold Spring Harbor Press, Cold Spring Harbor, N.Y.), and Ausubel et al., *CURRENT PROTOCOLS IN MOLECULAR BIOLOGY* (1994), (Greene Publishing Associates and John Wiley & Sons, New York, N.Y.). under the current regulations described in United States Dept. of *HHS, NATIONAL INSTITUTE OF HEALTH (NLH) GUIDELINES FOR RECOMBINANT DNA RESEARCH*. These references include procedures for the following standard methods: cloning procedures with plasmids, transformation of host cells, cell culture, plasmid DNA purification, phenol extraction of DNA, ethanol precipitation of DNA, agarose gel electrophoresis, purification of DNA fragments from agarose gels, and restriction endonuclease and other DNA-modifying enzyme reactions.

Expression in Bacterial Cells

Control elements for use in bacteria include promoters, optionally containing operator sequences, and ribosome binding sites. Useful promoters include sequences derived from sugar metabolizing enzymes, such as galactose, lactose (lac) and maltose. Additional examples include promoter sequences derived from biosynthetic enzymes such as tryptophan (trp), the β-lactamase (bla) promoter system, bacteriophage λPL, and T7. In addition, synthetic promoters can be used, such as the tac promoter. The β-lactamase and lactose promoter systems are described in Chang et al., *Nature* (1978) 275: 615, and Goeddel et al., *Nature* (1979) 281: 544; the alkaline phosphatase, tryptophan (trp) promoter system are described in Goeddel et al., *Nucleic Acids*

Res. (1980) 8: 4057 and EP 36,776 and hybrid promoters such as the tac promoter is described in U.S. Pat. No. 4,551,433 and de Boer et al., *Proc. Natl. Acad. Sci. USA* (1983) 80: 21–25.

However, other known bacterial promoters useful for expression of eukaryotic proteins are also suitable. A person skilled in the art would be able to operably ligate such promoters to the coding sequences of interest, for example, as described in Siebenlist et al., *Cell* (1980) 20: 269, using linkers or adaptors to supply any required restriction sites. Promoters for use in bacterial systems also generally will contain a Shine-Dalgarno (SD) sequence operably linked to the DNA encoding the target polypeptide. For prokaryotic host cells that do not recognize and process the native target polypeptide signal sequence, the signal sequence can be substituted by a prokaryotic signal sequence selected, for example, from the group of the alkaline phosphatase, penicillinase, Ipp, or heat stable enterotoxin II leaders. The origin of replication from the plasmid pBR322 is suitable for most Gram-negative bacteria.

The foregoing systems are particularly compatible with *Escherichia coli*. However, numerous other systems for use in bacterial hosts including Gram-negative or Gram-positive organisms such as *Bacillus* spp., *Streptococcus* spp., *Streptomyces* spp., *Pseudomonas* species such as *P. aeruginosa*, *Salmonella typhimurium*, or *Serratia marcescans*, among others. Methods for introducing exogenous DNA into these hosts typically include the use of $CaCl_2$ or other agents, such as divalent cations and DMSO. DNA can also be introduced into bacterial cells by electroporation, nuclear injection, or protoplast fusion as described generally in Sambrook et al. (1989), MOLECULAR CLONING: A LABORATORY MANUAL, 2d edition (Cold Spring Harbor Press, Cold Spring Harbor, N.Y.). These examples are illustrative rather than limiting. Preferably, the host cell should secrete minimal amounts of proteolytic enzymes. Alternatively, in vitro methods of cloning, e.g., PCR or other nucleic acid polymerase reactions, are suitable.

Prokaryotic cells used to produce the target polypeptide of this invention are cultured in suitable media, as described generally in Sambrook et al. (1989), MOLECULAR CLONING: A LABORATORY MANUAL, 2d edition (Cold Spring Harbor Press, Cold Spring Harbor, N.Y.).

Expression in Yeast Cells

Expression and transformation vectors, either extrachromosomal replicons or integrating vectors, have been developed for transformation into many yeasts. For example, expression vectors have been developed for, among others, the following yeasts: *Saccharomyces cerevisiae*, as described in Hinnen et al., *Proc. Natl. Acad. Sci. USA* (1978) 75: 1929; Ito et al., *J. Bacteriol.* (1983) 153: 163; *Candida albicans* as described in Kurtz et al., *Mol. Cell. Biol.* (1986) 6: 142; *Candida maltosa*, as described in Kunze et al., *J. Basic Microbiol.* (1985)25: 141; *Hansenula polymorpha*, as described in Gleeson et al., *J. Gen. Microbiol.* (1986) 132: 3459 and Roggenkamp et al., *Mol. Gen. Genet.* (1986) 202 :302); *Kluyveromyces fragilis*, as described in Das et al., *J. Bacteriol.* (1984) 158: 1165; *Kluyveromyces lactis*, as described in De Louvencourt et al., *J. Bacteriol.* (1983) 154: 737 and Van den Berg et al., *Bio/Technotogy* (1990) 8: 135; *Pichia guillerimondii*, as described in Kunze et al., *J. Basic Microbiol.* (1985) 25: 141; *Pichia pastoris*, as described in Cregg et al., *Mol. Cell. Biol.* (1985) 5: 3376 and U.S. Pat. Nos. 4,837,148 and 4,929,555; *Schizosaccharomyces pombe*, as described in Beach and Nurse, *Nature* (1981) 300: 706; and *Yarrowia lipolytica*, as described in Davidow et al., *Curr. Genet.* (1985) 10: 380 and Gaillardin et al., *Curr. Genet.* (1985) 10: 49, *Aspergillus* hosts such as *A. nidulans*, as described in Ballance et al., *Biochem. Biophys. Res. Commun.* (1983) 112: 28289; Tilbum et al., *Gene* (1983) 26: 205–221 and Yelton et al., *Proc. Natl. Acad. Sci. USA* (1984) 81: 1470–1474, and *A. niger*, as described in Kelly and Hynes, *EMBO J.* (1985) 4: 475479; *Trichoderma reesia*, as described in EP 244,234, and filamentous fungi such as, e.g., *Neurospora, Penicillium, Tolypocladium*, as described in WO 91/00357.

Control sequences for yeast vectors are known and include promoters regions from genes such as alcohol dehydrogenase (ADH), as described in EP 284,044, enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK), as described in EP 329,203. The yeast PHO5 gene, encoding acid phosphatase, also provides useful promoter sequences, as described in Myanohara et al., *Proc. NatL Acad. Sci. USA* (1983) 80: 1. Other suitable promoter sequences for use with yeast hosts include the promoters for 3-phosphoglycerate kinase, as described in Hitzeman et al., *J. Biol. Chem.* (1980) 255: 2073, or other glycolytic enzymes, such as pyruvate decarboxylase, triosephosphate isomerase, and phosphoglucose isomerase, as described in Hess et al., *J. Adv. Enzyme Reg.* (1968) 7: 149 and Holland et al., *Biochemistry* (1978) 17:4900. Inducible yeast promoters having the additional advantage of transcription controlled by growth conditions, include from the list above and others the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman, EP 073,657. Yeast enhancers also are advantageously used with yeast promoters. In addition, synthetic promoters which do not occur in nature also function as yeast promoters. For example, upstream activating sequences (UAS) of one yeast promoter may be joined with the transcription activation region of another yeast promoter, creating a synthetic hybrid promoter. Examples of such hybrid promoters include the ADH regulatory sequence linked to the GAP trascription activation region, as described in U.S. Pat. Nos. 4,876,197 and 4,880,734. Other examples of hybrid promoters include promoters which consist of the regulatory sequences of either the ADH2, GAL4, GAL10, or PHO5 genes, combined with the transcriptional activation region of a glycolytic enzyme gene such as GAP or PyK, as described in EP 164,556. Furthermore, a yeast promoter can include naturally occurring promoters of non-yeast origin that have the ability to bind yeast RNA polymerase and initiate transcription.

Other control elements which may be included in the yeast expression vectors are terminators, for example, from GAPDH and from the enolase gene, as described in Holland et al., *J. Biol. Chem.* (1981) 256: 1385, and leader sequences which encode signal sequences for secretion. DNA encoding suitable signal sequences can be derived from genes for secreted yeast proteins, such as the yeast invertase gene as described in EP 012,873 and JP 62,096,086 and the a-factor gene, as described in U.S. Pat. Nos. 4,588,684, 4,546,083 and 4,870,008; EP 324,274; and WO 89/02463. Alternatively, leaders of non-yeast origin, such as an interferon leader, also provide for secretion in yeast, as described in EP 060,057.

Methods of introducing exogenous DNA into yeast hosts are well known in the art, and typically include either the transformation of spheroplasts or of intact yeast cells treated with alkali cations.

Transformations into yeast can be carried out according to the method described in Van Solingen et al., *J. Bact.* (1977) 130:946 and Hsiao et al., *Proc. Natl. Acad. Sci. (USA)* (1979) 76:3829. However, other methods for introducing DNA into cells such as by nuclear injection, electroporation, or protoplast fusion may also be used as described generally in Sambrook et al., cited above.

For yeast secretion the native target polypeptide signal sequence may be substituted by the yeast invertase, α-factor, or acid 5-phosphatase leaders. The origin of replication from the 2μ plasmid origin is suitable for yeast. A suitable selection gene for use in yeast is the trp1 genre present in the yeast plasmid described in Kingsman et al., *Gene* (1979) 7: 141 or Tschemper et al., *Gene* (1980) 10:157. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 Gene.

For intracellular production of the present polypeptides in yeast, a sequence encoding a yeast protein can be linked to a coding sequence of the polypeptide to produce a fusion protein that can be cleaved intracellularly by the yeast cells upon expression. An example, of such a yeast leader sequence is the yeast ubiquitin gene.

Extression in Insect Cells

Baculovirus expression vectors (BEVs) are recombinant insect viruses in which the coding sequence for a foreign gene to be expressed is inserted behind a baculovirus promoter in place of a viral gene, e.g., polyhedrin, as described in Smith and Summers, U.S. Pat. No., 4,745,051.

An expression construct herein includes a DNA vector useful as an intermediate for the infection or transformation of an insect cell system the vector generally containing DNA coding-for a baculovirus transcriptional promoter, optionally but preferably, followed downstream by an insect signal DNA sequence capable of directing secretion of a desired protein, and a site for insertion of the foreign gene encoding the foreign protein, the signal DNA sequence and the foreign gene being placed under the transcriptional control of a baculovirus promoter, the foreign gene herein being the coding sequence of the polypeptide.

The promoter for use herein can be a baculovirus transcriptional promoter region derived from any of the over 500 baculoviruses generally infecting insects, such as, for example, the Orders Lepidoptera, Diptera, Orthoptera, Coleoptera and Hymenoptera including, for example, but not limited to the viral DNAs of *Autographo californica* MNPV, *Bombyx mori* NPV, *rrichoplusia ni* MNPV, *Rachlplusia ou* MNPV or *Galleria mellonella* MNPV. Thus, the baculovirus transcriptional promoter can be, for example, a baculovirus immediate-early gene IEI or IEN promoter, an immediate-early gene in combination with a baculovirus delayed-early gene promoter region selected from the group consisting of a 39K and a HindIII fragment containing a delayed early gene; or a baculovirus late gene promoter. The immediate-early or delayed ery promoters can be enhanced with transcriptional enhancer elements.

Particularly suitable for use herein is the strong polyhedrin promoter of the baculovirus, which directs a high level of expression of a DNA insert, as described in Friesen et al. (1986) "The Regulation of Baculovirus Gene Expression" in: THE MOLECULAR BIOLOGY OF BACULOVIRUSES (W.Doerfler, ed.): EP 127,839 and EP 155,476; and the promoter from the gene encoding the p10 protein, as described in Vlak et al., *J. Gen. Virol.* (1988) 69:765–776.

The plasmid for use herein usually also contains the polyhedrin polyadenylation signal, as described in Miller et al., *Ann. Rev. Microbiol.* (1988) 42:177 and a procaryotic ampicillin-resistance (amp) gene and an origin of replication for selection and propagation in *E. coli*. DNA encoding suitable signal sequences can also be included and is generally derived from genes for secreted insect or baculovirus proteins, such as the baculovirus polyhedrin gene, as described in Carbonell et al., *Gene* (1988) 73:409, as well as mammalian signal sequences such as those derived from genes encoding human a-interferon as described in Maeda et al., *Nature* (1985) 315:592–594; human gastrin-releasing peptide, as described in Lebacq-Verheyden et al., *Mol. Cell. Biol.* (1988) 8: 3129; human IL-2, as described in Smith et al., *Proc. Natl. Acad. Sci. USA* (1985) 82:8404; mouse IL-3, as described in Miyajima et al., *Gene* (1987) 58:273; and human glucocerebrosidase, as described in Martin et al., *DNA* (1988) 7:99.

Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified and can be used herein. See, for example, the description in Luckow et al., *Bio/Technology*(1988) 6: 47–55, Miller et al., in GENETIC ENGINEERING (Setlow, J.K. et al. eds.), Vol. 8 (Plenum Publishing, 1986), pp. 277–279, and Maeda et al., *Nature*, (1985) 315: 592–594. A variety of such viral strans are publicly available, e.g., the L-1 variant of *Autographa californica* NPV and the Bm-5 strain of *Bombyx mori* NPV. Such viruses may be used as the virus for transfection of host cells such as *Spodoptera frugiperda* cells.

Other baculovirus genes in addition to the polyhedrin promoter may be employed to advantage in a baculovirus expression system. These include immediate-early (alpha), delayed-early (beta), late (gamma), or very late (delta), according to the phase of the viral infection during which they are expressed. The expression of these genes occurs sequentially, probably as the result of a "cascade" mechanism of transcriptional regulation. Thus, the immediate-early genes are expressed immediately after infection, in the absence of other viral functions, and one or more of the resulting gene products induces transcription of the delayed-early genes. Some delayed-early gene products, in turn, induce transcription of late genes, and finally, the very late genes are expressed under the control of previously expressed gene products from one or more of the earlier classes. One relatively well defined component of this regulatory cascade is IEI, a preferred immediate-early gene of *Autographo californica* nuclear polyhedrosis virus (AcMNPV). IEI is pressed in the absence of other viral functions and encodes a product that stimulates the transcription of several genes of the delayed-early class, including the preferred 39K gene, as described in Guarino and Summers, *J. Virol.* (1986) 57:563–571 and *J. Virol.* (1987) 61:2091–2099 as well as late genes, as described in Guanno and Summers, *Virol.* (1988) 162:4441 51.

Immediate-early genes as described above can be used in combination with a baculovirus gene promoter region of the delayed-early category. Unlike the immediate-early genes, such delayed-early genes require the presence of other viral genes or gene products such as those of the immediate-early genes. The combination of immmediate-early genes can be made with any of several delayed-early gene promoter regions such as 39K or one of the delayed-early gene promoters found on the HindIII fragment of the baculovirus genome. In the present instance, the 39 K promoter region can be linked to the foreign gene to be expressed such that expression can be further controlled by the presence of IEI, as described in L. A. Guarino and Summers (1986a), cited above; Guarino & Summers (1986b) *J. Virol.*, (1986) 60:215–223, and Guarino et al. (1986c), *J. Virol.* (1986) 60:224–229.

Additionally, when a combination of immediate-early genes with a delayed-early gene promoter region is used, enhancement of the expression of heterologous genes can be realized by the presence of an enhancer sequence in direct cis linkage with the delayed-early gene promoter region. Such enhancer sequences are characterized by their enhancement of delayed-early gene expression in situations where the immediate-early gene or its product is limited. For example, the hr5 enhancer sequence can be linked directly, in cis, to the delayed-early gene promoter region, 39K, thereby enhancing the expression of the cloned heterologous DNA as described in Guarino and Summers (1986a), (1986b), and Guarino et al. (1986).

The polyhedrin gene is classified as a very late gene. Therefore, trnscription from the polyhedrin promoter requires the previous expression of an unknown, but probably large number of other viral and cellular gene products. Because of this delayed expression of the polyhedrin promoter, state-of-the-art BEVs, such as the exemplary BEV system described by Smith and Summers in, for example, U.S. Pat. No., 4,745,051 will express foreign genes only as a result of gene expression from the rest of the viral genome, and only after the viral infection is well underway. This represents a limitation to the use of existing BEVs. The ability of the host cell to process newly synthesized proteins decreases as the baculovirus infection progresses. Thus, gene expression from the polyhedrin promoter occurs at a time when the host cell's ability to process newly synthesized proteins is potentially diminished for certain proteins such as human tissue plasminogen activator. As a consequence, the expression of secretory glycoproteins in BEV systems is complicated due to incomplete secretion of the cloned gene product, thereby trapping the cloned gene product within the cell in an incompletely processed form.

While it has been recognized that an insect signal sequence can be used to express a foreign protein that can be cleaved to produce a mature protein, the present invention is preferably practiced with a mammalian signal sequence appropriate for the gene expressed.

An exemplary insect signal sequence suitable herein is the sequence encoding for a Lepidopteran adipokinetic hormone (AKH) peptide. The AKH family consists of short blocked neuropeptides that regulate energy substrate mobilization and metabolism in insects. In a preferred embodiment, a DNA sequence coding for a Lepidopteran *Manduca sexta* AKH signal peptide can be used. Other insect AKH signal peptides, such as those from the Orthoptera *Schistocerca gregaria* locus can also be employed to advantage. Another exemplary insect signal sequence is the sequence coding for Drosophila cuticle proteins such as CP1, CP2, CP3 or CP4.

Currently, the most commonly used transfer vector that can be used herein for introducing foreign genes into AcNPV is pAc373. Many other vectors, known to those of skill in the art, can also be used herein. Materials and methods for baculovirus/insect cell expression systems are commercially available in a kit form from companies such as Invitrogen (San Diego Calif.) ("MaxBac" kit). The techniques utilized herein are generally known to those skilled in the art and are fully described in Summers and Smith, A MANUAL OF METHODS FOR BACULOVIRUS VECTORS AND INSECT CELL CULTURE PROCEDURES, Texas Agricultural Experiment Station Bulletin No. 1555, Texas A&M University (1987); Smith et al. *Mol. Cell. Biol.* (1983) 3: 2156, and Luckow and Summers (1989). These include, for example, the use of pVL985 which alters the polyhedrin start codon from ATG to ATT, and which introduces a BamHI cloning site 32 basepairs downstream from the ATT, as described in Luckow and Summers, *Virology* (1989) 17:31.

Thus, for example, for insect cell expression of the present polypeptides, the desired DNA sequence can be inserted into the transfer vector, using known techniques. An insect cell host can be cotransformed with the transfer vector containing the inserted desired DNA together with the genomic DNA of wild type baculovirus, usually by cotransfection. The vector and viral genome are allowed to recombine resulting in a recombinant virus that can be easily identified and purified. The packaged recombinant virus can be used to infect insect host cells to express a desired polypeptide.

Other methods that are applicable herein are the standard methods of insect cell culture, cotransfection and preparation of plasmids are set forth in Summers and Smith (1987), cited above. This reference also pertains to the standard methods of cloning genes into AcMNPV transfer vectors, plasmid DNA isolation, transferring genes into the AcmMNPV genome, viral DNA purification, radiolabeling recombinant proteins and preparation of insect cell culture media. The procedure for the cultivation of viruses and cells are described in Volkman and Summers, *J. Virol.* (1975) 19:820–832 and Volkian, al., *J. Virol.* (1976) 19:820–832.

Expression in Mammalian Cells

Typical promoters for mammalian cell expression of the polypeptides of the invention include the SV40 early promoter, the CMV promoter, the mouse mammary tumor virus LTR promoter, the adenovirus major late promoter (Ad MLP), and the herpes simplex virus promoter, among others. Other non-viral promoters, such as a promoter derived from the murine metallothionein gene, will also find use in mammalian constructs. Mammalian expression may be either constitutive or regulated (inducible), depending on the promoter. Typically, transcription termination and polyadenylation sequences will also be present, located 3' to the translation stop codon. Preferably, a sequence for optimization of initiation of translation, located 5' to the polypeptide coding sequence, is also present Examples of transcription terminator/polyadenylation signals include those derived from SV40, as described in Sambrook et al. (1989), cited previously. Introns, containing splice donor and acceptor sites, may also be designed into the constructs of the present invention.

Enhancer elements can also be used herein to increase expression levels of the mammalian constructs. Examples include the SV40 early gene enhancer, as described in Dijkema et al, *EMBO J.* (1985) 4:761 and the enhancer/promoter derived from the long terminal repeat (LTR) of the Rous Sarcoma Virus, as described in Gorman et al., *Proc. Natl. Acad. Sci. USA* (1982b) 79:6777 and human cytomegalovirus, as described in Boshart et al., *Cell* (1985) 41:521. A leader sequence can also be present which includes a sequence encoding a signal peptide, to provide for the secretion of the foreign protein in mammalian cells. Preferably, there are processing sites encoded between the leader fragment and the gene of interest such that the leader sequence can be cleaved either in vivo or in vitro. The adenovirus tripartite leader is an example of a leader sequence that provides for secretion of a foreign protein in mammalian cells.

Once complete, the mammalian expression vectors can be used to transform any of several mammalian cells. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. General aspects of mammalian cell host system transformations have been described by Axel in U.S. Pat. No. 4,399,216.

The mammalian host cells used as responsive cells or producing cells in the invention may be cultured in a variety of media Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, or 4,560,655, WO 90/103430, WO 87/00195. and U.S. RE 30,985, may be used as culture media for the host cells. Any of these media may be supplemented as necessary to create optimal conditions for the function of the cells according to the method of the invention, including supplementation as necessary with hormones and/or other growth factors such as insulin, transferrin, or epidermal growth factor, salts (such as sodium chloride, calcium, magnesium, and phosphate), buffers (such as HEPES), nucleosides (such as adenosine and thymidine), antibiotics (such as Gentamycin™M drug), trace elements (defined as inorganic compounds usually present at final concentrations in the micromolar range), and glucose or an equivalent energy source range). Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Gene therapy strategies for delivery of constructs of the invention can utilize viral or non-viral vector approaches in in vivo or ex vivo modality. Expression of such coding sequence can be induced using endogenous mammalian or heterologous promoters. Expression of the coding sequence in vivo can be either constitutive or regulated.

For delivery using viral vectors, any of a number of viral vectors can be used, as described in Jolly, *Cancer Gene Therapy* 1: 51–64 (1994). For example, the coding sequence can be inserted into plasmids designed for expression in retroviral vectors, as described in Kimura et al., *Human Gene Therapy* (1994) 5: 845–852, adenoviral vectors, as described in Connelly et al., *Human Gene Therapy* (1995) 6: 185–193, adeno-associated viral vectors, as described in Kaplitt et al., *Nature Genetics* (1994) 6: 148–153 and sindbis vectors. Promoters that are suitable for use with these vectors include the Moloney retroviral LTR, CMV promoter and the mouse albumin promoter. Replication incompetent free virus can be produced and injected directly into the animal or humans or by transduction of an autologous cell ex vivo, followed by injection in vivo as described in Zatioukal et al., *Proc. Natl. Acad. Sci. USA* (1994) 91: 5148–5152.

The altered coding sequence can also be inserted into plasmid for expression of the uPAR polypeptide in vivo or ex vivo. For in vivo therapy, the coding sequence can be delivered by direct injection into tissue or by intravenous infusion. Promoters suitable for use in this manner include endogenous and heterologous promoters such as CMV. Further, a synthetic T7T7OB promoter can be constructed in accordance with Chen et al. (1994), *Nucleic Acids Res.* 22: 2114–2120, where the T7 polymerase is under the regulatory control of its own promoter and drives the transcription of the uPAR coding sequence, which is also placed under the control of a T7 promoter. The coding sequence can be injected in a formulation comprising a buffer that can stablize the coding sequence and facilitate transduction thereof into cells and/or provide targeting, as described in Zhu et al., *Science* (1993) 261: 209–211.

Expression of the coding sequence in vivo upon delivery for gene therapy purposes by either viral or non-viral vectors can be regulated for maximal efficacy and safety by use of regulated gene expression promoters as described in Gossen et al., *Proc. Natl. Acad. Sci. USA* (1992) 89:5547–5551. For example, the uPAR coding sequence can be regulated by tetracycline responsive promoters. These promoters can be regulated in a positive or negative fashion by treatment with the regulator molecule.

For non-viral delivery of the coding sequence, the sequence can be inserted into conventional vectors that contain conventional control sequences for high level expression, and then be incubated with synthetic gene transfer molecules such as polymeric DNA-binding cations like polylysine, protamnine, and albumin, linked to cell targeting ligands such as asialoorosomucoid, as described in Wu and Wu, *J. Biol. Chem.* (1987) 262: 4429–4432; insulin, as described in Hucked et al., *Biochem. Pharmacol.* 40: 253–263 (1990); galactose, as described in Plank et al., *Bioconjugate Chem.* 3:533–539 (1992); lactose, as described in Midoux et al., *Nucleic Acids Res.* 21: 871–878 (1993); or transferrin, as described in Wagner et al., *Proc. Natl. Acad. Sci. USA* 87:3410–3414 (1990). Other delivery systems include the use of liposomes to encapsulate DNA comprising the uPAR gene under the control of a variety of tissue-specific or ubiquitously-active promoters, as described in Nabel et al., *Proc. Natl. Acad. Sci. USA* 90: 11307–11311 (1993), and Philip et al., *Mol. Cell Biol.* 14: 2411–2418 (1994). Further non-viral delivery suitable for use includes mechanical delivery systems such as the biolistic approach, as described in Woffendin et al., *Proc. Natl. Acad. Sci. USA* (1994) 91(24): 11581–11585. Moreover, the uPAR coding sequence and the product of expression of such can be delivered through deposition of photopolymerized hydrogel materials. Other conventional methods for gene delivery that can be used for delivery of the uPAR coding sequence include, for example, use of hand held gene transfer particle gun, as described in U.S. Pat. No. 5,149, 655; use of ionizing radiation for activating transferred gene, as described in U.S. Pat. No. 5,206,152 and PCT application WO92/11033.

Application of gene therapy technology with regard to the peptides and polypeptides of the invention and their analogues or variants can be made in disease states where, for example, activity of any of uPAR is detrimental to the patien. It is also conceived by the inventors that gene therapy using the polypeptides and peptides of the invention and their analogues or variants is appropriate when treating conditions of cytoskeletal disruption, for example, in vivo expression of antagonists or dominant negatives to interupt, for example, the uPAR:integrin binding pair formation and the cellular responses, such as cellular migration, that result from the binding pair formation of uPAR and integrin.

In general, gene therapy can be applied according to the invention in all situations where uPAR forms a binding pair interaction with vitronectin or integrin and acts to modulate cytoskeletal integrity and affect cellular migration, by administering according to a gene therapy protocol, of a sufficient amount of a peptide of the invention or its analogue, variant, or dominant negative, for example, for modulating the normal activity of uPAR binding pair interactions.

Applications of the peptides of the invention, whether administered by a gene therapy protocol, or otherwise, can be made in the context of treatment of a patient afflicted by a condition characterized by cytoskeletal disruption and/or also including cellular migration. Conditions of cancer and/or inflammatory conditions are examples of such conditions.

For the purpose of the invention, based on the sequence and function of the novel peptides herein, assays can be developed for screening small molecule library pools for functional uPAR:vitronectin and uPAR:integrin inhibitors, antagonists, and agonists for use in controlling, for example, cytoskeletal disruption and cellular migration. These inhibitors, antagonists, or agonists can be administered to the animal, and can be administered with a pharmaceutically acceptable carrier, including, for example, liposomes compositions such as Depofoam™, and other carriers such as, for example, Focalgel™.

Small molecule libraries may be used to screen for the ability of the small molecule to mimic, synergize or attenuate any action of SIP, and can be made as follows. A "library" of peptides may be synthesized and used following the methods disclosed in U.S. Pat. No. 5,010,175, (the '175 patent) and in PCT WO91/17823. In method of the '175 patent, a suitable peptide synthesis support, for example, a resin, is coupled to a mixture of appropriately protected, activated amino acids.

The method described in WO91/17823 is similar. However, instead of reacting the synthesis resin with a mixture of activated amino acids, the resin is divided into twenty equal portions, or into a number of portions corresponding to the number of different amino acids to be added in that step, and each amino acid is coupled individually to its portion of resin. The resin portions are then combined, mixed, and again divided into a number of equal portions for reaction with the second amino acid. Additionally, one may maintain separate "subpools" by treating portions in parallel, rather than combining all resins at each step. This simplifies the process of determining which peptides are responsible for any observed alteration of gene expression in a responsive cell.

The methods described in WO91/17823 and U.S. Pat. No. 5,194,392 enable the preparation of such pools and subpools by automated techniques in parallel, such that all synthesis and resynthesis may be performed in a matter of days.

A further alternative agents include small molecules, including peptide analogs and derivatives, that can act as stimulators or inhibitors of gene expression, or as ligands or antagonists. Some general means contemplated for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, Weinstein, B. ed., Marcell Dekker, Inc., publ. New York (1983). Moreover, substitution of D-amino acids for the normal L-stereoisomer can be carried out to increase the half-life of the molecule.

Peptoids, polymers comprised of monomer units of at least some substituted amino acids, can act as small molecule stimulators or inhibitors herein and can be synthesized as described in PCT 91/19735. Presently preferred amino acid substitutes are N-alkylated derivatives of glycine, which are easily synthesized and incorporated into polypeptide chains. However, any monomer units which allow for the sequence specific synthesis of pools of diverse molecules are appropriate for use in producing peptoid molecules. The benefits of these molecules for the purpose of the invention is that they occupy different conformational space than a peptide and as such are more resistant to the action of proteases.

Peptoids are easily synthesized by standard chemical methods. The preferred method of synthesis is the "submonomer" technique described by R. Zuckermann et al., *J. Am. Chem. Soc.* (1992) 114:10646–7. Synthesis by solid phase techniques of heterocyclic organic compounds in which N-substituted glycine monomer units forms a backbone is described in copending application entitled "Synthesis of N-Substituted Oligomers" filed on Jun. 7, 1995 and is herein incorporated by reference in full. Combinatorial libraries of mixtures of such heterocyclic organic compounds can then be assayed for the ability to alter gene expression.

Synthesis by solid phase of other heterocyclic organic compounds in combinatorial libraries is also described in copending application U.S. Ser. No. 08/485,006 entitled "Combinatorial Libraries of Substrate-Bound Cyclic Organic Compounds" filed on Jun. 7, 1995, herein incorporated by reference in full. Highly substituted cyclic structures can be synthesized on a solid support by combining the submonomer method with powerful solution phase chemistry. Cyclic compounds containing one, two, three or more fused rings are formed by the submonomer method by first synthesizing a linear backbone followed by subsequent intramolecular or intermolecular cyclization as described in the same application.

Suitable carriers for the therapeutics of the invention for administration in a patient, including but not limited to molecules capable of antagonizing the inhibitory effects of the peptides of the imvention (for example peptides 7, 9, 18, and 25 and analogs or variants of these), including, for example small molecules, peptides, peptoids, polynucleotides and polypeptides, may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991). Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier. The term "liposomes" refers to, for example, the liposome compositions described in U.S. Pat. No. 5,422,120, WO 95/13796, WO 94/23697, WO 91/14445 and EP 524,968 B1. Liposomes may be pharmaceutical carriers for the peptides, polypeptides or polynucleotides of the invention, or for combination of these therapeutics.

Further objects, features, and advantages of the present invention will become apparent from the following detailed description. It should be understood, however, that the detailed description, while indicating preferred embodiments of the present invention, is given by way of illustration only, since various changes and modifications within the spirit and scope of the invention will become apparent to those skilled in the art from this detailed description. The invention is also not limited to any theories of action of the elements of the invention.

EXAMPLE 1

Affinity Selection of 15 mer Random Peptide Library on uPAR:uPA1–48 Complexes

Soluble recombinant human urokinase receptor (suPAR) was expressed and secreted from baculovirus-infected Sf9 insect cells, as described in Goodson et al., Proc. Natl. Acad.Sci.USA 91:7129–7133 (1994). The EGF-like domain of human urokinase (uPA residues 1–48) was expressed from recombinant yeast as described Stratton-Thomas et al., Prot.Eng. 8: 463–470 (1995). UPA1–48 was purified by a revision of the published procedure, involving ion exchange chromatography and reverse phase HPLC under reducing conditions, followed by a refolding step and rechromatography on reversed phase HPLC of the oxidized material. Soluble uPAR was purified on a column of immobilized uPA1–48, eluted at low pH, biotinylated according to Kaufman et al. Anal. Biochem. 211:261–266 (1993) and purified on a Soft-Avidin column (Promega Corporation, Madison, Wis.). The uPAR fragment encompassing domains 2 and 3 (amino acids 93–313) with a C-terminal epitope tag of E-Y-M-P-M-E (SEQ ID NO:18 as described in Grussenmeyer et al. Proc. Natl. Acad. Sci. USA 82: 7952–7954 (1985) was expressed in baculovirus infected Sf9 insect cells, and purified from the conditioned media by affinity chromatography on an anti-epitope antibody column. Peptides were synthesized at Chiron Mimotopes (Melbourne, Australia) with fee amino terrnini and amidated carboxyl termini, and were greater than 70% pure by HPLC and MS analysis. A variant of clone 20 peptide was prepared with the sequence: AE PMPHSLNFSQYAWYT (SEQ ID NO:7). A scrambled version of clone 7 had the sequence: VEYRDAYSYPQYLSYLE (SEQ ID NO:8). Recombinant PAI-1 was obtained from American Diagnostica. Horseradish peroxidase (HRP) conjugated streptavidin was from Pierce Chemical, Rockford, Ill. Anti-M13 antibody was from Pharmacia, Piscataway, N.J.

Affinity selections were performed on streptavidin coated magnetic beads (Dynal, Rochester, N.Y.) Biotinylated suPAR (1.5 µg) was mixed with 3.5 µg of uPA1–48 in a total volume of 100 µl for 30 minutes at room temperature. Magnetic beads were blocked with PBS/1% BSA (PSB/BSA) for 30 minutes and then suPAR:uPA1–48 complexes were added in PBS/0.1% BSA, and incubated at room temperature for 2 hours. Beads were then washed 3 times with PBS/BSA and resuspended with an aliquot of the 15 mer random peptide library in 500 µl. For comparison an identical aliquot of the beads was incubated with the parent bacteriophage vector (LP67, as described in Devlin et al, Science 249: 404 406 (1990). Binding of bacteriophage was for 45 minutes at room temperature followed by 7 washes with 2 ml PBS/BSA and elution of bound bacteriophage with 500 µl 60 mM glycine, 1.5 M urea, pH 2.5. Eluted bacteriophage were titered and amplified as described in Goodson et al, Proc.Natl.Acad.Sci. USA 91: 7129–7133 (1994), and Devlin et al, Science 249: 404–406 (1990). Amplified bacteriophage were then selected for additional rounds on suPAR:uPA1–48 complexes as described above. DNA sequencing was performed on PCR amplified inserts from individual bacteriophage plaques by the dideoxy method.

EXAMPLE 2

Bacteriophaae Binding to sUPAR

Streptavidin, 100 µl (0.1 mg/ml) in 50 mM $Na_2CO_3$, pH 9.6, was added to MaxiSorp wells (Nunc), incubated overnight at 4 C, and then washed with PBS/BSA. Biotinylated sUPAR (25 nM in PBS/BSA) was added to the wells and incubated for 2 hours at room temperature prior to washing. Competitive peptide inhibitors were added to the wells immediately prior to addition of the bacteriophage. The wells were incubated for one hour at room temperature, then washed and bound bacteriophage eluted with 6M urea in 0.1N HCl, pH 2.5. After 15 minutes, the urea eluate was brought to neutral pH by addition of 2M Tris base and the bacteriophage titers of input stocks and elutions measured by plaque formation assay. Results were expressed as the percent of input bacteriophage which bind to the wells. Alternatively, the amount of bacteriophage was determined in an ELISA where phage were preincubated with HRP-conjugated anti-M13 antibody for 30 minutes at room temperature before dispensing into wells prepared as above and incubated for one hour at room temperature. The final anti-M13 conjugate dilution was 1:4000. After washing, TMB substrate (100 µl/well) was added and color development was stopped with 0.8N $H_2SO_4$ (100 µl/well). The absorbance at 450 nm was then measured in a 96 well plate reader.

Novel peptide sequences are obtained by panning uPA1–48:uPAR complexes. Selection of high affinity peptide ligands for the uPA binding site on uPAR was a relatively efficient process as described in Goodson et al, Proc. Natl. Acad. Sci. USA 91: 7129–7133 (1994), was extended by selecting for peptide-displaying bacteriophage with affinity for additional, functionally important sites on uPAR by including an excess of recombinant EGF-like domain of uPA (uPA1–48) to reduce selection of uPA binding site peptides as described in Stratton-Thomas et al, Prot. Eng. 8: 463470 (1995). The EGF-like domain is the receptor binding motif as described in Appella et al, J. Biol. Chem. 262: 4437–4440 (1987) and Robbiati et al Fibrinol. 4: 53–60 (1990), and binds to uPAR with similar affinity (0.1–5 nM) as uPA as described in Mazar et al, Fibrinol. 6: 49–55 (1992). The 15 mer random peptide bacteriophage library as descrobed in Devlin et al, Science 249: 404–406 (1990) was affinity selected on suPAR:uPA1–48 complexes immobilized on magnetic beads. The yield of bacteriophage increased 30 fold, from 0.008% at round 2 to 0.24% at round 3 suggesting enrichment for binding bacteriophage.

Twenty-eight independent bacteriophage were isolated and the random peptide encoding DNA segments sequenced. From these 28 bacteriophage, 23 different sequences were obtained, but only four clones (7, 9, 18, and 25) had substantial yields (>2%), when individually affinity selected on immobilized sUPAR. This is in contrast to previous results of affinity selection on uPAR alone, where the majority of selected bacteriophage bound with substantial yield as described in Goodson et al, *Proc.Natl.Acad.Sci. USA* 91: 7129–7133 (1994). The yields of these four bacteriophage were determined on suPAR in the presence and absence of uPA1–48. In addition, the encoded peptides were synthesized and tested as competitors in a suPAR binding assay as described in Stratton-Thomas et al, *Prot.Eng.* 8: 463–470 (1995), and Kaufman et al *Anal.Biochem.* 211: 261–266 (1993). These results are summarized in the Table in FIG. 6.

The binding of the selected bacteriophage was largely unaffected by the presence of a 1000 fold molar excess of uPA1–48. In contrast, the previously described bacteriophage (clone 20 and uPA13–32) which bind to the uPA binding site, both gave yields of 2–5% on suPAR but were reduced to background levels (greater than 500-fold reduction) in the presence of uPA1–48, as reported in Goodson et al, *Proc.Natl.Acad.Sci. USA* 91: 7129–7133 (1994). These results suggest that the bacteriophage selected on uPA1–48: uPAR complexes represent distinct classes of uPAR ligands from clone 20 and uPA13–32.

It was also shown by the inventors that bacteriophage bound to sUPAR domain 2–3 fragment. Protein G, 100μl, 1 mg/ml in 50 mM $Na_2CO_3$, pH9.6, was added to MaxiSorp wells, incubated overnight at 4° C. and then washed with PBS/BSA. Fifty μl of monoclonal antibody to the epitope tag EYMPME (SEQ ID NO: 18) was added at 1 mg/ml in PBS/BSA and incubated for 2 hours at room temperature. The wells were washed, recombinant sUPAR domain 2–3 (1.7 μM in PBS/BSA) was added and incubated for 1.5 hours at room temperature. The wells were washed prior to the addition of bacteriophage (approximately $10^8$ pfu), and then treated as described in the previous section for binding to suPAR.

EXAMPLE 3

Vitronectin Binding Assay

Vitronectin was purified from human plasma by the method of Yatohgo et al, *Cello Struct.and Funct.* 13: 281–292 (1988). Purified vitronectin was diluted to 20 μg/ml in PBS containing 1 mM $CaCl_2$ and 0.5 mM $MgCl_2$, dispensed at 50 μl/well into Immulon II wells (Dynatech, Chantilly, Va.), incubated overnight at 4° C. and washed with PBS/BSA. Biotinylated sUPAR was diluted to 20 nM in PBS/BSA, incubated with or without test ligand for 30 minutes at room temperature (22° C.), dispensed at 100 μl/well and incubated for 90 minutes. Wells were then washed and horseradish peroxidase (HRP)-conjugated streptavidin was added at 0.4 μg/ml in PBS/2% BSA for 1 hour followed by washing and addition of 100 μl/well TMB substrate. The color development was stopped with 100 μl of 0.8N $H_2SO_4$ and the absorbance at 450 nm measured in a 96 well plate reader (Dynatech, Chantilly, Va.). Antagonistic effects of test ligands were measured as described above except the ligands were incubated with 20 nM biotinylated suPAR in the presence of 20 nM uPA1–48.

It was found that uPA1–48:uPAR complexes bind with high affinity to vitronectin. In order to analyze the effects of the various peptide ligands on the uPAR:vitronectin interaction, we developed an in vitro ELISA based assay for this interaction, in which biotinylated suPAR and uPA1–48 bind to immobilized, urea purified vitronectin, and the bound sUPAR is detected with HRP conjugated streptavidin. Under the conditions of the assay binding of biotinylated uPAR to vitronectin is strictly dependent on uPA1–48, as shown in FIG. 1. The apparently stoichiometric binding of the uPA1–48:suPAR complexes to vitronectin indicates that the affinity of this interaction is higher than the concentration of complex (Kd<20 nM).

It was also found that bacteriophage derived peptides block complex binding and cell adhesion to vitronectin. The ability of the various bacteriophage derived peptides to affect binding of uPA1–48:uPAR complexes to vitronectin was assessed in the ELISA assay. Two classes of peptides were effective antagonists in this assay. First, clone 20 and uPA13–32, which compete directly for uPA1–48 binding to sUPAR, reduced binding. An analog of clone 20 peptide, which shows greatly reduced receptor binding activity did not affect binding to vitronectin. Second, clones 7 and 18, which show greatly reduced competition for uPA1–48 binding (see Table in FIG. 6) also inhibit complex binding, while a scrambled version of clone 7 did not. None of the peptides when tested alone increased the binding of biotinylated suPAR to vitronectin. A third peptide, clone 25, which bound efficiently to suPAR as a bacteriophage, had little or no effect on uPA1–48 stimulated vitronectin binding. In order to test whether the clone 7 and 18 peptides bound directly at the vitronectin binding site on uPAR, and inhibited vitronectin binding by uPAR:uPA1–48 by direct competition for that site, the inventors examined the effects of vitronectin on the binding of these bacteriophage. Vitronectin reduced bacteriophage binding to the uPA1–48:suPAR complex by 5–10 fold, consistent with the hypothesis that these peptides mimic vitronectin as a uPAR ligand.

Previous results had shown that vitronectin binding by uPAR correlated with cell adhesion of stimulated U937 cells as described in Wei et al, *J. Biol. Chem.* 269: 32380–32388 (1994). It was found also that clone 7 peptide could block uPAR mediated adhesion of these cells, whereas the scrambled version of the same peptide had no effect.

Additionally, binding of uPA1–48:uPAR complexes to vitronectin was shown to be blocked by PAI-1, vitronectin, and the somatomedin B domain of vitronectin. Another function of vitronectin has been determined to be stabilization of the active conformation of PAI-1, which appears to occur via the somatomedin B domain of vitronectin, as described in Seiffert et al *J. Biol. Chem.* 269: 2659–2666 (1994). PAI-1 is a very efficient competitor of uPA1–48: suPAR complexes binding to vitronectin, with an apparent IC50 of 10 nM. This suggested to the inventors that the binding site of uPAR and PAI-1 are overlapping. It has been demonstrated previously that high affinity vitronectin binding to active PAI-1 is primarily via the somatomedin B domain, as described in Seiffert et al *J. Biol. Chem.* 269: 2659–2666 (1994). Thus, the inventors tested whether vitronectin and recombinant somatomedin B domain would also inhibit uPAR binding to vitronectin. Accordingly, the inventors showed that molecules inhibit, whereas a point mutation of the domain does not.

It was also then determined that the bacteriophage peptides are homologous to the somatomedin B domain of vitronectin, which is also the binding site of PAI-1. The sequences of bacteriophage derived peptides 7 and 18 were examined for homology to this domain. As shown in FIG 3, there is a conserved motif, LXXArY (where X is a hydrophilic residue, and AR=F,Y) between residues 24–28 of the somatomedin B domain and clone 7 and 18 peptides. In addition, clones 7 and 18 share the sequence E-L-d just N-terminal to the conserved leucine, whereas the related sequence D-E-L is found in the somatomedin B domain of vitronectin at residues 22–24, adjacent to the conserved sequence LCSYY (SEQ ID NO: 9).

To determine which residues in peptide 7 are important for uPAR binding and inhibition of vitronectin binding, we replaced each residue separately with alanine, and tested the resulting peptides for inhibition of bacteriophage binding to uPAR, and blockade of the binding of uPA1–48:uPAR complexes to vitronectin. The results shown in FIG. 4, indicate that the residues conserved between the peptides and vitronectin are important for activity in these assays.

EXAMPLE 4

SuPAR:1-Anilino-8-Napthalenesulfonate (ANS) Fluorescence Measurements

Determination of the effect of various peptide ligands on sUPAR/ANS fluorescence was performed following a procedure similar to that of Ploug et al, *Biochem.* 33: 8991–8997 (1994). Fluorescence emission spectra of sUPAR/ANS solutions with or without competitors were obtained using an Hitachi F-4500 fluorescence spectrophotometer with an excitation wavelength of 386 nm, 5-nm band-pass excitation and emission slits, and a 10 mm path length quartz cuvette. The emission spectra from 400 to 600 nm were recorded. For competition measurements, dilutions of a stock sUPAR/ANS solution were made to give individual 0.5 ml aliquots with a final concentration of 2 µM sUPAR, 10 µM ANS, and 0 to 20 µM competitor in PBS containing 10% DMSO. Fluorescence measurements were made after a one hour incubation at 25° C.

It was found that ANS fluorescence enhancement distinguished the peptide sequences To further analyze the binding sites of these peptide ligands the inventors examined their effects on the fluorescence enhancement of ANS which occurs upon uPAR binding, and which has been shown to correlate with occupancy of the uPA binding site and the functional state of the uPAR molecule of Ploug et al, *Biochem.* 33: 8991–8997 (1994). The effects of several peptide uPAR ligands on ANS fluorescence enhancement in the presence of uPAR had the expected result that uPA1–48 and clone 20 reduce ANS fluorescence, consistent with their potent activity in the receptor binding assay. Clone 7 also reduced fluorescence in a dose dependent manner, although at higher concentrations, while clone 25 peptide has no effect at up to 20 µM. These results suggested that clone 7, 20, and uPA1–48 share some common binding determinants or a common binding conformation of uPAR with ANS, whereas clone 25 binds to a distinct site.

EXAMPLE 5

Recombinant UPAR Domain2–3 Fragment Binds Bacteriophage but not uPA1–48

UPAR is the only member of the Ly6/CD59 family to contain three repeats of the homologous cysteine containing domain as described in Plough et al, *FEBS Lett.* 349: 163–168 (1994). Previous work by the inventors suggested that the binding site for vitronectin on uPAR is in domains 2 and 3 (D23) as described by Wei et al, *J. Biol. Chem.* 269: 32380–32388 (1994). To further address this question we expressed in baculovirus infected Sf9 insect cells a fragment of suPAR, residues 93–313, predicted to encompass the second and third CD59 homologous domains with a C-terminal 6 amino acid epitope tag. The secreted protein was purified on an anti-epitdpe affinity column, and was tested first for its ability to compete in the suPAR binding assay. There was no competition in this assay at 100 nM D23, in contrast to intact suPAR which shows an IC50 of 0.1 nM under the same conditions.

The inventors then tested the ability of various uPAR bacteriophage displayed ligands to bind to immobilized D23. The results shown in FIG. 5, indicate that the ligands fall into three different classes with respect to binding to D23 and sUPAR. Clone 20 and 13–32 bind signficantly only to intact suPAR, whereas clones 9 and 25 bind equivalently to the D23 fragment and full-length receptor. Bacteriophage bearing clones 7 and 18 peptides show an intermediate degree of binding to D23, and substantially better binding to intact receptor.

EXAMPLE 6

Identification of uPAR:Integrin Binding and Binding Site

In order to ascertain whether cytoskeletal connecting elements important to integrin-dependent adhesion were also involved in adhesion mediated by uPAR, embryonic kidney cells (293 cells) were engineered to coexpress uPAR along with a chimeric protein comprised of the β1 cytoplasmic tail fused with the transmembrane domain of complementarity determining region 4 (CD4). Expression of this chimeric β1 construct has previously been shown to exert a dominant negative effect on integrin-mediated adhesion by sequestering cytoplasmic elements which bind β chains as described in Lukashev et al, *J. Biol. Chem.* 26: 18311 (1994). Co-expression of uPAR with β1 cytoplasmic domains completely abrogated uPAR-dependent vitronectin adhesion. Clones expressing full length or truncated β1 cytoplasmic tails prepared as in Lukashev et al, *J. Biol. Chem.* 26: 18311 (1994) were transfected with cDNA for GPI-uPAR and selected as in Wei et al, *J. Biol. Chem.* 169: 32380 (1994). Chimeric β1 expression was induced by cadmium for 6 hours prior to assaying adhesion to vitronectin at 37° C. Following induction of full length β1 chimerics, essentially no cells were adherent to vitronectin-coated surfaces whereas co-transfectants expressing the truncated β1 adhered avidly.

Cells co-expressing uPAR with a control, truncated β1 cytoplasmic domain unable to connect with cytoskeletal proteins as described in Lukashev et al *J. Biol. Chem.* 26: 18311 (1994) adhered normally. Inhibition of adhesion at 37° C. developed despite comparable urokinase and vitronectin binding at 4° C. among the co-transfectants, suggesting competition between β1 cytoplasmic tails and uPAR for cytoskeletal connecting elements important to adhesion.

Based on these results, immunoprecipitation experiments were conducted to determine whether uPAR was physically associated with native β1 integrins. A stable transfectant expressing a chimeric uPAR comprised of the extracellular domain of uPAR fused with the IL-2R alpha transmembrane domain and short cytoplasmic tail (TM-uPAR) was generated as a control. This chimeric uPAR binds urokinase comparably to GPI-uPAR as described in Hui et al, J. Biol. Chem. 269:8153 (1994) The full length cDNA for the human urokinase receptor and human interleukin-2 receptor were isolated from human macrophages and human T cells, respectively, by reverse transcription and polymerase chain reaction. A chimeric cDNA construct encoding the extracellular domains of the uPAR (amino acids 1–281) and the transmembrane/cytoplasmic domams of IL-2R alhpa (amino acids 218–251) was prepared. The chimeric cDNA was subcloned into pBluescript, verified by nucleotide sequenceing (Sequenase, United States Biochemical Corp) then digested with XbaI and XhoI and finally subcloned into the pCEP4 expression vector. Co-transfectants were shown to bind equivalent amounts of vitronectin and urokinase at 4° C. by methods as described in Wei et al, J. Biol. Chem. 269: 32380(1994).

Immunoblotting confirmed comparable expression of GPI-uPAR and TM-uPAR in 293 cells as well as comparable urokinase and vitronectin binding. When triton X 100 (0.2%) insoluble fraction of GPI-uPAR 293 cells is solubilized in polar detergents, immunoprecipitation of β1 clearly co-precipitates uPAR as described in Filardo et al, *J. Cell. Biol.* 1995, in press: Cells ($5\times10^6$) were cultured overnight, washed twice with microtubule stabilization buffer (0.1M PIPES, pH 6.9, 2M glycerol, 1 mM EDTA, and 1 mM magnesium acetate), and then extracted on ice for 5 minutes in buffer containing 0.2% Triton X 100 and inhibitors (1 mM sodium orthovandate, 1 mM phenylsulfonyl fluoride, 10 mg/ml leupeptin). The insoluble residues were soluboized at 4° C. for 20 minutes in 1× RIPA buffer (150 mM sodium chloride, 50 mM Tris-HCl, pH 7.5, 1% deoxycholate, 0.1% sodium dodecyl sulfate, 1% Triton X-100) supplemented with protease inhibitors. The triton soluble fraction was diluted 1:1 with 2× RIPA buffer. Both fractions were centrifuged for 10 minutes at 6000 rpm, and then precleared by incubation with nonimmune serum and protein A-agarose for 2 hours at 4° C.

Supernatants were transferred to fresh tubes and incubated with antibodies against β1 or caveolin for 2 hours at 4° C. Immune complexes were recovered with protein A-agarose. The washed immunoprecipitates were subjected to 8% SDS-PAGE, and transferred onto a nitrocellulose membrane. The filters were blocked in 5% nonfat dried milk, and probed with anti-uPAR Mab R2 (from E. Ronne, Finsen Lab, Denmark), 1 µg/ml. The blots were washed and incubated with HRP conjugated antibodies for one hour. After washing, the membranes were developed using enhanced chemiluminescence (NEN Du Pont, Wilmington, Del.) according to the manufacturer's protocol.

A similar result was obtained when a rat monoclonal β1 antibody was substituted. β1 immuno-precipitations of the triton X 100 detergent soluble fraction revealed no uPAR. In addition, much less or no association of uPAR with β1 could be demonstrated with TM-uPAR in either triton fraction.

Cell adhesion assays were conducted to determin whether the observed uPAR/β1/caveolin complexes were functionally relevant. Although both GPI-uPAR and TM-uPAR bound vitronectin comparably at 4° C., only GPI-uPAR expressing cells showed enhanced adhesion to vitronectin, suggesting that the association of uPAR with β1 is necessary.

To test this hypothesis further, a phage display peptide library was screened for uPAR-binding phages. A number of phage peptides were isolated as described in Goodson et al, *Proc. Natl. Acad. Sci. U.S.A.* 91: 7129 (1994). One phage displayed a uPAR-binding peptide which neither blocked urokinase/uPAR or vitronectin/uPAR associations. This peptide, peptide 25 and several controls were synthesized, purified, and screened for their effect on adhesion. Peptide 25, but not the controls, was found to abrogate GPI-uPAR dependent adhesion of 293 cells to vitronectin, $IC_{50}$ of about 60 µM. Peptide 25 had no effect on adhesion to fibronectin by nontransfected 293 cells. Immunoprecipitation experiments were then conducted to assess the effect of this and control peptides on the association of uPAR with β1. Peptide 25, but not a control peptide, largely disrupted the β1/caveolin/uPAR complexes at concentrations which blocked adhesion (100 µM). Several additional non-inhibitory peptides from the original screening were tested and found to have no effect on β1/uPAR co-precipitation, confirming that the β1/GPI-uPAR/caveolin complexes operate as an adhesive unit.

In addition, minimal motifs for peptide 25 were determined by an alanine scan of peptide 25, looking for binding to uPAR:

| residue changes to alanine | % inhibition of phage binding |
|---|---|
| NONE (clone 25) | 100 |
| S-1 | 99 |
| T-2 | 69 |
| Y-3 | 21 |
| H-4 | 17 |
| H-5 | 100 |
| L-6 | 0 |
| S-7 | 99 |
| L-8 | 96 |
| G-9 | 16 |
| Y-10 | 16 |
| M-11 | 35 |
| Y-12 | 17 |
| T-13 | 39 |
| L-14 | 98 |
| N-15 | 100 |

These data suggest that the minimal motif necessary for inhibition of binding is YHXLXXGYMYT (SEQ ID NO 5) in clone 25 where X is any amino acid.

These data indicate that uPAR associates with and modifies function of certain integrins. This association both promotes adhesion to a migration toward a specific matrix protein, vitronectin, and destabilizes the normal adhesive function of integrins. In vivo, the ability of uPAR to destabilize integrin-dependent attachments is reinforced by the concurrent binding of the protease urokinase.

EXAMPLE 7

Identification of Additional Ligands that Bind to uPAR

In a uPAR binding assay, the following analogs were tested in a competition with phage displaying either peptide 25 or peptide 9. The analogs comprise both natural and unnatural amino acids.

In the table below, the analog sequences are listed with the amino terminus of the analogs printed on the left. The analog sequences utilized the one letter amino acid abbreviations unless otherwise noted. The lower case letters indicate a D-amino acids. for example "s" indicates a D-serine. Analogs 2–4 and 31–96 have a free amino terminus and a C-terminal carboxamides. Analogs 5–30 comprise an acetylated terminus (Ac-oligomer-NH$_2$).

The analogs were tested in an assay utilizing soluble uPAR, similar to the method described in Example 2. The analogs were tested for their ability to compete with phage displaying either peptide 9 or peptide 25. Analogs 3–61 were tested in competition with peptide 25. Analogs 62–96 were tested in competition with peptide 9. Approximately $10^8$ plaque forming units of the phage were used in the assay.

| # | Sequence | # | Sequence |
|---|---|---|---|
|  |  | 49 | AEStYHHLSLGYMYTLN |
|  |  | 50 | AESTyHHLSLGYMYTLN |
| 3 | AESTYHHLSLGYMYTLN | 51 | AESTYhHLSLGYMYTLN |
| 4 | AESTYHHLSLGYMYTLN | 52 | AESTYHhLSLGYMYTLN |
| 5 | AESTYHHLSLGYMYTLN | 53 | AESTYHHlSLGYMYTLN |
| 6 | AESTYHHLSLGYMYTL | 54 | AESTYHHLsLGYMYTLN |
| 7 | AESTYHHLSLGYMYT | 55 | AESTYHHLSlGYMYTLN |
| 8 | AESTYHHLSLGYMY | 56 | AESTYHHLSLGyMYTLN |
| 9 | AESTYHHLSLGYM | 57 | AESTYHHLSLGYmYTLN |
| 10 | AESTYHHLSLGY | 58 | AESTYHHLSLGYMyTLN |
| 11 | AESTYHHLSLG | 59 | AESTYHHLSLGYMYtLN |
| 12 | AESTYHHLSL | 60 | AESTYHHLSLGYMYTlN |
| 13 | AESTYHHLS | 61 | AESTYHHLSLGYMYTLn |
| 14 | AESTYHHL | 62 | AEFFKLGPNGYVYLHSA |
| 15 | ESTYHHLSLGYMYTLN | 63 | AEFFKLGPNGYVYLHSA |
| 16 | STYHHLSLGYMYTLN | 64 | AEFFKLGPNGYVYLHSA |
| 17 | TYHHLSLGYMYTLN | 65 | AAFFKLGPNGYVYLHSA |
| 18 | YHHLSLGYMYTLN | 66 | AEAFKLGPNGYVYLHSA |
| 19 | HHLSLGYMYTLN | 67 | AEFAKLGPNGYVYLHSA |
| 20 | HLSLGYMYTLN | 68 | AEFFALGPNGYVYLHSA |
| 21 | LSLGYMYTLN | 69 | AEFFKAGPNGYVYLHSA |
| 22 | SLGYMYTLN | 70 | AEFFKLAPNGYVYLHSA |
| 23 | LGYMYTLN | 71 | AEFFKLGANGYVYLHSA |
| 24 | AESTYHHLSLG | 72 | AEFFKLGPAGYVYLHSA |
| 25 | ESTYHHLSLGY | 73 | AEFFKLGPNAYVYLHSA |
| 26 | STYHHLSLGYM | 74 | AEFFKLGPNGAVYLHSA |
| 27 | TYHHLSLGYMY | 75 | AEFFKLGPNGYAYLHSA |
| 28 | YHHLSLGYMYT | 76 | AEFFKLGPNGYVALHSA |
| 29 | HHLSLGYMYTL | 77 | AEFFKLGPNGYVYAHSA |
| 30 | HLSLGYMYTLN | 78 | AEFFKLGPNGYVYLASA |
| 31 | AESTYHHGPNGYMYTLN | 79 | AEFFKLGPNGYVYLHAA |
| 32 | AESTYHHsPNGYMYTLN | 80 | AEFFKLsPNGYVYLHSA |
| 33 | AESTYHHaPNGYMYTLN | 81 | AEFFKLaPNGYVYLHSA |
| 34 | AESTFHHLSLGYMYTLN | 82 | aEFFKLGPNGYVYLHSA |
| 35 | AESTXHHLSLGYMYTLN | 83 | AeFFKLGPNGYVYLHSA |
| 36 | AEST?HHLSLGYMYTLN | 84 | AEfFKLGPNGYVYLHSA |
| 37 | AESTYHHLSLGFMYTLN | 85 | AEFfKLGPNGYVYLHSA |
| 38 | AESTYHHLSLGXMYTLN | 86 | AEFFkLGPNGYVYLHSA |
| 39 | AESTYHHLSLG?MYTLN | 87 | AEFFKlGPNGYVYLHSA |
| 40 | AESTYHHLSLGYMFTLN | 88 | AEFFKLGpNGYVYLHSA |
| 41 | AESTYHHLSLGYMXTLN | 89 | AEFFKLGPnGYVYLHSA |
| 42 | AESTYHHLSLGYM?TLN | 90 | AEFFKLGPNGyVYLHSA |
| 43 | AESTYHHLSLGYVYTLN | 91 | AEFFKLGPNGYvYLHSA |
| 44 | AESTYHHLSLGYJYTLN | 92 | AEPFKLGPNGYVyLHSA |
| 45 | AESTYHHLSLGTbYTLN | 93 | AEFFKLGPNGYVYlHSA |
| 46 | aESTYHHLSLGYMYTLN | 94 | AEFFKLGPNGYVYLhSA |
| 47 | AeSTYHHLSLGYMYTLN | 95 | AEFFKLGPNGYVYLHsA |
| 48 | AEsTYHHLSLGYMYTLN | 96 | AEFFKLGPNGYVYLHSa |

X = Fmoc-L-Nal-OH.0.5H2O (L1Napthylalanine)
? = Fmoc-L-2-Nal-OH (L2Napthylalanine)
J = L-Norleucine
b = alpha-aminobutyric acid Results of Analogs 3–30

The analogs were tested at a concentration at 40 µM in the uPAR competition assay with phage displaying peptide 25. The results below show which analogs were active.

| Sequence | Active? @ 40 µM |
|---|---|
| A E S T̂ Ⓨ Ⓗ H Ⓛ S L Ⓖ Ⓨ Ⓜ Ⓨ Ⓣ L N | Y |
| A E S T Y H H L S L G Y M Y T L | Y |
| A E S T Y H H L S L G Y M Y T | Y |
| A E S T Y H H L S L G Y M Y | N |
| A E S T Y H H L S L G Y M | N |
| A E S T Y H H L S L G Y | N |
| A E S T Y H H L S L G | N |
| A E S T Y H H L S L | N |
| A E S T Y H H L S | N |
| A E S T Y H H L | N |
| E S T Y H H L S L G Y M Y T L N | Y |
| S T Y H H L S L G Y M Y T L N | Y |
| T Y H H L S L G Y M Y T L N | Y |
| Y H H L S L G Y M Y T L N | Y |
| H H L S L G Y M Y T L N | N |
| H L S L G Y M Y T L N | N |
| L S L G Y M Y T L N | N |
| S L G Y M Y T L N | N |
| L G Y M Y T L N | N |
| A E S T Y H H L S L G | N |
| E S T Y H H L S L G Y | N |

-continued

| Sequence | Active? @ 40 μM |
|---|---|
| S T Y H H L S L G Y M | N |
| T Y H H L S L G Y M Y | N |
| Y H H L S L G Y M Y T | Y |
| H H L S L G Y M Y T L | N |
| H H L S L G Y M Y T L | N |

Results of Analogs 31–61

Analogs 31–61 were tested for their ability to compete with phage displaying peptide 25. The active analogs were tested further at two concentrations, 5 μM and 2.5 μM. These concentrations were calculated based on the synthesis reactions. However, the sequences * were further tested and determined to contain high amounts of amino acids and the quantity tested could have been higher than 5 μM or 2.5 μM.

The results of the testing with the active analogs are shown below:

| Sequence | % Inhibition | |
|---|---|---|
| | 5 uM | 2.5 uM |
| A E S Ṫ (Y) (H) H (L) S L (G) (Y) (M) (Y) (T) L N | 59 | 45 |
| A E S T (F) H H L S L G Y M Y T L N | 47 | 38 |
| A E S T (X) H H L S L G Y M Y T L N | 94 | 70 |
| A E S T (?) H H L S L G Y M Y T L N | 78 | 61 |
| A E S T Y H H L S L G Y (V) Y T L N | 82 | 63 |
| A E S T Y H H L S L G Y (J) Y T L N | 91 | 84* |
| A E S T Y H H L S L G Y (b) Y T L N | 59 | 31 |
| (a) E S T Y H H L S L G Y M Y T L N | 57 | 41 |
| A (e) S T Y H H L S L G Y M Y T L N | 61 | 35 |
| A E S T Y H H L (a) L G Y M Y T L N | 86 | 73 |
| A E S T Y H H L S (I) G Y M Y T L N | 80 | 56 |
| A E S T Y H H L S L G Y M Y T (I) N | 75 | 22 |
| A E S T Y H H L S L G Y M Y T L (a) | 55 | 32 |

X = Fmoc-L-Nal-OH.0.5H₂O--
? = Fmoc-L-2-Nal-OH
J = L-Norleucine
b = alpha-aminobutyric acid Results of Oligomers 62–79

An alanine scan was performed using the sequence of peptide 9. The sequences of analogs 62–79 are the same as peptide 9 except an alanine residue was substituted at one position in the sequence. Analogs 62–79 are all the possible alanine substitutions into peptide 9.

The results of the Ala scan show that alanine substitution for Leu at position 6, Tyr at position 11, Val at position 12, and Tyr at position 13 destroyed receptor binding activity. Alanine substitution at for Glu at position 2, Phe at position 4, or Leu at position 14 decreased but did not destroy, the receptor binding activity of the oligomers as compared to peptide 9.

Results of Analogs 80–96

Analogs 80–96 were tested for their ability to compete with phage displaying peptide 9. The active analogs were tested further at two concentrations, 5 μM and 2.5 μM. These concentrations were calculated based on the synthesis reactions. However, the sequences * were further tested and determined to contain low amounts of amino acids and the quantity tested could have been lower than 5 μM or 2.5 μM.

The results of the testing with the active analogs are shown below:

| Sequence | % Inhibition | |
|---|---|---|
| | 5 uM | 2.5 uM |
| A Ė F F K (L) G P N G (Y) (V) (Y) L̇ H S A | 71 | 59 |
| A E F F K L G P N (a) Y V Y L H S A | 95 | 89 |
| A E F F K L G P N (a) Y V Y L H S A | 80 | 79 |
| (a) E F F K L G P N G Y V Y L H S A | 41 | 24* |
| A (e) F F K L G P N G Y V Y L H S A | 59 | 44 |
| A E F F K L G (p) N G Y V Y L H S A | 76 | 80* |
| A E F F K L G P (n) G Y V Y L H S A | 13 | 15 |
| A E F F K L G P N G Y V (Y) L H S A | 3.3 | 8.5 |
| A E F F K L G P N G Y V Y L (h) S A | 41 | 36 |
| A E F F K L G P N G Y V Y L H (s) A | 59 | 47 |
| A E F F K L G P N G Y V Y L H S (a) | 40 | 38* |

What is claimed is:

1. An isolated peptide that binds a urokinase plasnminogen activator receptor (uPAR) and inhibits uPAR binding to vitronectin, wherein the isolated peptide comprises an amino acid sequence selected from the group consisting of AEPVYQYELDSYLRSYY (SEQ ID NO:1), and AELDLSTFYDIQYLLRT (SEQ ID NO: 3).

2. An isolated peptide that binds a urokinase plasminogen activator receptor (uPAR), comprising an amino acid sequence selected from the group consisting of AEFFKLGPNGYVYLHSA (SEQ ID NO:2) and FKLXXXGYVYL (SEQ ID NO:6 where X is any amino acid.

3. A pharmaceutical composition for treating a patient with a disorder characterized by upregulation of uPA and uPAR comprising an effective amount of a peptide that comprises an amino acid sequence selected from the group consisting of AEPVYQYELDSYLRSYY (SEQ ID NO: 1), AEFFKLGPNGYVYLHSA (SEQ ID NO:2), AELDLSTFYDIQYLLRT (SEQ ID NO:3), and FKLXXXGYVYL (SEQ ID NO:6), where X is any amino acid.

4. The pharmaceutical composition of claim 3, wherein the pharmaceutically acceptable camer comprises one selected from the group consisting of a liposome, a gel, a polymer matrix, a foam, and a buffer.

* * * * *

SEQUENCE LISTING

<160> NUMBER OF SEQ ID NOS: 76

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 1

Ala Glu Pro Val Tyr Gln Tyr Glu Leu Asp Ser Tyr Leu Arg Ser Tyr
 1               5                  10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 2

Ala Glu Phe Phe Lys Leu Gly Pro Asn Gly Tyr Val Tyr Leu His Ser
 1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 3

Ala Glu Leu Asp Leu Ser Thr Phe Tyr Asp Ile Gln Tyr Leu Leu Arg
 1               5                  10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 4

Ala Glu Ser Thr Tyr His His Leu Ser Leu Gly Tyr Met Tyr Thr Leu
 1               5                  10                  15

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide ligand
<220> FEATURE:
<221> NAME/KEY: MOD_RES
<222> LOCATION: (3)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 5

-continued

```
Tyr His Xaa Leu Xaa Xaa Gly Tyr Met Tyr Thr
 1               5                  10
```

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide ligand
<220> FEATURE:
<221> NAME/KEY: MOD_RES
<222> LOCATION: (4)..(6)
<223> OTHER INFORMATION: Any amino acid

<400> SEQUENCE: 6

```
Phe Lys Leu Xaa Xaa Xaa Gly Tyr Val Tyr Leu
 1               5                  10
```

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 7

```
Ala Glu Pro Met Pro His Ser Leu Asn Phe Ser Gln Tyr Ala Trp Tyr
 1               5                  10                  15
```

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 8

```
Val Glu Tyr Arg Asp Ala Tyr Ser Tyr Pro Gln Tyr Leu Ser Tyr Leu
 1               5                  10                  15
```

<210> SEQ ID NO 9
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 9

```
Asp Gln Glu Ser Cys Lys Gly Arg Cys Thr Glu Gly Phe Asn Val Asp
 1               5                  10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp
                35                  40                  45
```

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 10

```
Ala Glu Pro Val Tyr Gln Tyr Glu Leu Asp Ser Tyr Leu Arg Ser Tyr
 1               5                  10                  15

Tyr

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 11

Ala Glu Leu Asp Leu Ser Thr Phe Tyr Asp Ile Gln Tyr Leu Leu Arg
 1               5                  10                  15

Thr

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 12

Ala Glu Pro Val Tyr Gln Tyr Glu Leu Asp Ser Tyr Leu Arg Ser Tyr
 1               5                  10                  15

Tyr

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 13

Ala Glu Phe Phe Lys Leu Gly Pro Asn Gly Tyr Val Tyr Leu His Ser
 1               5                  10                  15

Ala

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 14

Ala Glu Leu Asp Leu Ser Thr Phe Tyr Asp Ile Gln Tyr Leu Leu Arg
 1               5                  10                  15

Thr

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide ligand
```

```
<400> SEQUENCE: 15

Ala Glu Ser Thr Tyr His His Leu Ser Leu Gly Tyr Met Tyr Thr Leu
 1               5                  10                  15
Asn

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 16

Ala Glu Pro Met Pro His Ser Leu Asn Phe Ser Gln Tyr Leu Trp Tyr
 1               5                  10                  15
Thr

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide ligand

<400> SEQUENCE: 17

Cys Leu Asn Gly Gly Thr Ala Val Ser Asn Lys Tyr Phe Ser Asn Leu
 1               5                  10                  15
His Trp Cys

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: C-terminal
      epitope tag

<400> SEQUENCE: 18

Glu Tyr Met Pro Met Glu
 1               5

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Glu Ser Thr Tyr His His Leu Ser Leu Gly Tyr Met Tyr Thr
 1               5                  10                  15

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Glu Ser Thr Tyr His His Leu Ser Leu Gly Tyr Met Tyr
```

```
<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Glu Ser Thr Tyr His His Leu Ser Leu Gly Tyr Met
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Glu Ser Thr Tyr His His Leu Ser Leu Gly Tyr
 1               5                  10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Glu Ser Thr Tyr His His Leu Ser Leu Gly
 1               5                  10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Glu Ser Thr Tyr His His Leu Ser Leu
 1               5                  10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Glu Ser Thr Tyr His His Leu Ser
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 26

Ala Glu Ser Thr Tyr His His Leu
 1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Ser Thr Tyr His His Leu Ser Leu Gly Tyr Met Tyr Thr Leu Asn
 1               5                  10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Thr Tyr His His Leu Ser Leu Gly Tyr Met Tyr Thr Leu Asn
 1               5                  10                  15

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Tyr His His Leu Ser Leu Gly Tyr Met Tyr Thr Leu Asn
 1               5                  10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr His His Leu Ser Leu Gly Tyr Met Tyr Thr Leu Asn
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His His Leu Ser Leu Gly Tyr Met Tyr Thr Leu Asn
 1               5                  10

<210> SEQ ID NO 32

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Leu Ser Leu Gly Tyr Met Tyr Thr Leu Asn
  1               5                  10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Ser Leu Gly Tyr Met Tyr Thr Leu Asn
  1               5                  10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Leu Gly Tyr Met Tyr Thr Leu Asn
  1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Gly Tyr Met Tyr Thr Leu Asn
  1               5

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Glu Ser Thr Tyr His His Leu Ser Leu Gly
  1               5                  10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Glu Ser Thr Tyr His His Leu Ser Leu Gly Tyr
 1               5                  10
```

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Ser Thr Tyr His His Leu Ser Leu Gly Tyr Met
 1               5                  10
```

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Thr Tyr His His Leu Ser Leu Gly Tyr Met Tyr
 1               5                  10
```

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Tyr His His Leu Ser Leu Gly Tyr Met Tyr Thr
 1               5                  10
```

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
His His Leu Ser Leu Gly Tyr Met Tyr Thr Leu
 1               5                  10
```

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
His Leu Ser Leu Gly Tyr Met Tyr Thr Leu Asn
 1               5                  10
```

<210> SEQ ID NO 43
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 43

Ala Glu Ser Thr Tyr His His Gly Pro Asn Gly Tyr Met Tyr Thr Leu
 1               5                  10                  15

Asn

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Glu Ser Thr Tyr His His Ser Pro Asn Gly Tyr Met Tyr Thr Leu
 1               5                  10                  15

Asn

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Glu Ser Thr Tyr His His Ala Pro Asn Gly Tyr Met Tyr Thr Leu
 1               5                  10                  15

Asn

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Glu Ser Thr Phe His His Leu Ser Leu Gly Tyr Met Tyr Thr Leu
 1               5                  10                  15

Asn

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: L1-Napthylalanine

<400> SEQUENCE: 47

Ala Glu Ser Thr Xaa His His Leu Ser Leu Gly Tyr Met Tyr Thr Leu
 1               5                  10                  15

Asn
```

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: L2-Napthylalanine

<400> SEQUENCE: 48

Ala Glu Ser Thr Xaa His His Leu Ser Leu Gly Tyr Met Tyr Thr Leu
  1               5                  10                  15

Asn

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Glu Ser Thr Tyr His His Leu Ser Leu Gly Phe Met Tyr Thr Leu
  1               5                  10                  15

Asn

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: L1-Napthylalanine

<400> SEQUENCE: 50

Ala Glu Ser Thr Tyr His His Leu Ser Leu Gly Xaa Met Tyr Thr Leu
  1               5                  10                  15

Asn

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: L2-Napthylalanine

<400> SEQUENCE: 51

Ala Glu Ser Thr Tyr His His Leu Ser Leu Gly Xaa Met Tyr Thr Leu
  1               5                  10                  15

Asn

<210> SEQ ID NO 52
<211> LENGTH: 17
<212> TYPE: PRT

-continued

<213> ORGANISM: Artificial Sequence
<220> FEATURE:
<223> OTHER INFORMATION: Description of Artificial Sequence: Synthetic
      peptide

<400> SEQUENCE: 52

Ala Glu Ser Thr Tyr His His Leu Ser Leu Gly Tyr Met Phe Thr Leu
 1               5                  10                  15
Asn

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: L1-Napthylalanine

<400> SEQUENCE: 53

Ala Glu Ser Thr Tyr His His Leu Ser Leu Gly Tyr Met Xaa Thr Leu
 1               5                  10                  15
Asn

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: L2-Napthylalanine

<400> SEQUENCE: 54

Ala Glu Ser Thr Tyr His His Leu Ser Leu Gly Tyr Met Xaa Thr Leu
 1               5                  10                  15
Asn

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Glu Ser Thr Tyr His His Leu Ser Leu Gly Tyr Val Tyr Thr Leu
 1               5                  10                  15
Asn

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)

-continued

<223> OTHER INFORMATION: L-Norleucine

<400> SEQUENCE: 56

Ala Glu Ser Thr Tyr His His Leu Ser Leu Gly Tyr Xaa Tyr Thr Leu
 1               5                  10                  15
Asn

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: alpha-aminobutyric acid

<400> SEQUENCE: 57

Ala Glu Ser Thr Tyr His His Leu Ser Leu Gly Tyr Xaa Tyr Thr Leu
 1               5                  10                  15
Asn

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ala Phe Phe Lys Leu Gly Pro Asn Gly Tyr Val Tyr Leu His Ser
 1               5                  10                  15
Ala

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Glu Ala Phe Lys Leu Gly Pro Asn Gly Tyr Val Tyr Leu His Ser
 1               5                  10                  15
Ala

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Glu Phe Ala Lys Leu Gly Pro Asn Gly Tyr Val Tyr Leu His Ser
 1               5                  10                  15
Ala

<210> SEQ ID NO 61

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Glu Phe Phe Ala Leu Gly Pro Asn Gly Tyr Val Tyr Leu His Ser
 1               5                  10                  15

Ala

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Glu Phe Phe Lys Ala Gly Pro Asn Gly Tyr Val Tyr Leu His Ser
 1               5                  10                  15

Ala

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Glu Phe Phe Lys Leu Ala Pro Asn Gly Tyr Val Tyr Leu His Ser
 1               5                  10                  15

Ala

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Glu Phe Phe Lys Leu Gly Ala Asn Gly Tyr Val Tyr Leu His Ser
 1               5                  10                  15

Ala

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Glu Phe Phe Lys Leu Gly Pro Ala Gly Tyr Val Tyr Leu His Ser
 1               5                  10                  15

Ala
```

```
<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Glu Phe Phe Lys Leu Gly Pro Asn Ala Tyr Val Tyr Leu His Ser
 1               5                  10                  15

Ala

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Glu Phe Phe Lys Leu Gly Pro Asn Gly Ala Val Tyr Leu His Ser
 1               5                  10                  15

Ala

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Glu Phe Phe Lys Leu Gly Pro Asn Gly Tyr Ala Tyr Leu His Ser
 1               5                  10                  15

Ala

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Glu Phe Phe Lys Leu Gly Pro Asn Gly Tyr Val Ala Leu His Ser
 1               5                  10                  15

Ala

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Glu Phe Phe Lys Leu Gly Pro Asn Gly Tyr Val Tyr Ala His Ser
 1               5                  10                  15

Ala
```

-continued

```
<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Glu Phe Phe Lys Leu Gly Pro Asn Gly Tyr Val Tyr Leu Ala Ser
 1               5                  10                  15
Ala

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Glu Phe Phe Lys Leu Gly Pro Asn Gly Tyr Val Tyr Leu His Ala
 1               5                  10                  15
Ala

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Glu Phe Phe Lys Leu Ser Pro Asn Gly Tyr Val Tyr Leu His Ser
 1               5                  10                  15
Ala

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Glu Phe Phe Lys Leu Ala Pro Asn Gly Tyr Val Tyr Leu His Ser
 1               5                  10                  15
Ala

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Glu Phe Phe Lys Leu Gly Pro Asn Ser Tyr Val Tyr Leu His Ser
 1               5                  10                  15
Ala
```

```
<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Glu Phe Phe Lys Leu Gly Pro Asn Ala Tyr Val Tyr Leu His Ser
  1               5                  10                  15
Ala
```